US012734207B2

(12) United States Patent
Mehta et al.

(10) Patent No.: US 12,734,207 B2
(45) Date of Patent: *Sep. 15, 2026

(54) METHODS AND COMPOSITIONS FOR TREATING DYSBIOSIS OF ORAL MICROBIOME

(71) Applicant: Aveta Biomics, Inc., Bedford, MA (US)

(72) Inventors: Parag G. Mehta, Burlington, MA (US); Luis Z. Avila, Arlington, MA (US)

(73) Assignee: Aveta Biomics, Inc., Bedford, MA (US)

( * ) Notice: Subject to any disclaimer, the term of this patent is extended or adjusted under 35 U.S.C. 154(b) by 1044 days.

This patent is subject to a terminal disclaimer.

(21) Appl. No.: 17/599,585

(22) PCT Filed: Apr. 1, 2020

(86) PCT No.: PCT/US2020/026268

§ 371 (c)(1),
(2) Date: Sep. 29, 2021

(87) PCT Pub. No.: WO2020/206040

PCT Pub. Date: Oct. 8, 2020

(65) Prior Publication Data

US 2022/0193177 A1 Jun. 23, 2022

Related U.S. Application Data

(60) Provisional application No. 62/827,645, filed on Apr. 1, 2019.

(51) Int. Cl.

| | |
|---|---|
| ***A61K 35/741*** | (2015.01) |
| ***A61K 31/121*** | (2006.01) |
| ***A61K 35/742*** | (2015.01) |
| ***A61K 35/745*** | (2015.01) |
| ***A61K 36/9066*** | (2006.01) |
| ***A61P 1/00*** | (2006.01) |
| ***A61P 31/04*** | (2006.01) |

(52) U.S. Cl.

CPC ........ *A61K 36/9066* (2013.01); *A61K 31/121* (2013.01); *A61P 1/00* (2018.01); *A61P 31/04* (2018.01)

(58) Field of Classification Search

CPC .. A61K 36/9066; A61K 9/0056; A61K 45/06; A61K 31/12; A61P 1/00; A61P 31/04

See application file for complete search history.

(56) References Cited

U.S. PATENT DOCUMENTS

| | | | |
|---|---|---|---|
| 8,815,220 | B2 | 8/2014 | Pather et al. |
| 9,913,873 | B2 | 3/2018 | Thakkar |
| 10,105,419 | B2 | 10/2018 | Holstein et al. |
| 11,701,402 | B2 | 7/2023 | Mehta et al. |
| 2008/0193573 | A1 | 8/2008 | Gow et al. |
| 2008/0233218 | A1 | 9/2008 | Newmark et al. |
| 2014/0056828 | A1 | 2/2014 | Pather et al. |
| 2016/0151440 | A1 | 6/2016 | Gopi |
| 2016/0235803 | A1 | 8/2016 | Thakkar |
| 2016/0256513 | A1 | 9/2016 | May et al. |
| 2021/0252097 | A1 | 8/2021 | Mehta et al. |
| 2023/0321177 | A1 | 10/2023 | Mehta et al. |

FOREIGN PATENT DOCUMENTS

| | | | |
|---|---|---|---|
| WO | WO-2014/068597 | A2 | 5/2014 |
| WO | WO-2015/076430 | A1 | 5/2015 |
| WO | WO-2019/195349 | A1 | 10/2019 |
| WO | WO-2020/206040 | A1 | 10/2020 |

OTHER PUBLICATIONS

Inflammatory disorders from Merck Manual, pp. 1-4. Accessed Aug. 30, 2020. (Year: 2020).*

Inflammation from Merck Manual, pp. 1-3. Accessed Aug. 30, 2020. (Year: 2020).*

Merck Manual (https://www.merckmanuals.com/home/skin-disorders/fungal-skin-infections/overview-of-fungal-skin-infections accessed Feb. 19, 2019) (Year: 2019).*

Merck Manual (https://www.merckmanuals.com/professional/infectious-diseases/approach-to-parasitic-infections/approach-to-parasitic-infections?query=protozoa accessed Oct. 22, 2020 (Year: 2020).*

Merck Manual (https://www.merckmanuals.com/professional/infectious-diseases/viruses/overview-of-viruses accessed Feb. 19, 2019) (Year: 2019).*

National Institute of Health (https://www.niaid.nih.gov/research/antimicrobial-resistance-threats Feb. 11, 2020) (Year: 2020).*

Doron ("Bacterial infections: Overview"; International Encyclopedia of Public Heatlh, 2008:273-282) (Year: 2008).*

CDC fungal types (www.cdc.gov/fungal/diseases/index.html accessed May 21, 2021) (Year: 2021).*

Merck Manual Parasitic infections (https://www.merckmanuals.com/professional/infectious-diseases/approach-to-parasitic-infections/approach-to-parasitic-infections?query=protozoa accessed Oct. 22, 2020 (Year: 2020).*

National Institute of Cancer—understanding and related topics, accessed Aug. 21, 2014 at URL: cancer.gov/cancertopics/understandingcancer, 63 pages (Year: 2014).*

Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*

Merck Manuals Neuroblastoma accessed Mar. 12, 2017 at URL merckmanuals.com/professional/pediatrics/pediatric-cancers/neuroblastoma, 4 pages (Year: 2017).*

Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*

(Continued)

*Primary Examiner* — Julie Ha
*Assistant Examiner* — Kristina M Hellman
(74) *Attorney, Agent, or Firm* — Morse, Barnes-Brown & Pendleton, P.C.; Stanley F. Chalvire, Esq.; Erin E. Bryan, Esq.

(57) ABSTRACT

Disclosed are compositions and methods for treating or ameliorating dysbiosis of the oral microbiome.

23 Claims, 25 Drawing Sheets
(25 of 25 Drawing Sheet(s) Filed in Color)

(56) References Cited

OTHER PUBLICATIONS

Thyroid cancer accessed Mar. 12, 2017 at URL www.merckmanuals.com/professional/endocrine-and-metabolic-disorders/thyroid-disorders/thyroid-cancers, 4 pages (Year: 2017).*

Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*

Renal cell carcinoma, accessed Mar. 12, 2017 at URL merckmanuals.com/professional/genitourinary-disorders/genitourinary-cancer/renal-cell-carcinoma, 6 pages (Year: 2017).*

Merck Manual Overview of Leukemia accessed Aug. 21, 2014 at URL: merckmanuals.com/professional/hematology-and-oncology/leukemias/overview-of-leukemia, 2 pages (Year: 2014).*

Merck Manual Overview of Lymphoma accessed Aug. 21, 2014 at URL: merckmanuals.com/professional/blood-disorders/lymphomas/overview-of-lymphoma, 1 page. (Year: 2014).*

Jenkinson, "Beyond the oral microbiome," Environmental Microbiology 13:3077-3087 (2011) (Year: 2011).*

Mohammed et al., "Evaluation of antimicrobial activity of Curcumin against two oral bacteria," Automation, Control and Intelligent Systems 3: 18-21 (2015) (Year: 2015).*

Chang, et al., Immunomodulation of Curcumin on Adoptive Therapy with T Cell Functional Imaging in Mice, Cancer Prevention Research, vol. 5, No. 3, Mar. 2012, pp. 444-452.

Singh et al. "Quantum curcumin mediated inhibition of gingipains and mixed-biofilm of *Porphyromonas gingivalis* causing chronic periodontitis." *RSC Adv.*, 2018, 8, 40426-40445.

Lim, et al. "Oral Microbiome: A New Biomarker Reservoir for Oral and Oropharyngeal Cancers." *Theranostics* 2017; 7(17): 4313-4321.

International Search Report issued in International Application No. PCT/US2019/025465 dated Jun. 14, 2019.

International Search Report issued in International Application No. PCT/US2020/026268 dated Jun. 29, 2020.

Non-Final Office Action issued in U.S. Appl. No. 17/044,696 dated May 12, 2022.

Shengkai, et al., "Inhibitory Effect of Curcumin on Oral Carcinoma CAL-27 Cells Via Suppression of Notch-1 and NF-kappa B Signaling Pathways", *Journal of Cellular Biochemistry*, 112(4): 1055-1065 (2011).

Sood, et al., "Role of Curcumin in Systemic and Oral Health: An Overview", *Journal of Natural Science, Biology and Medicine*, 4(1): 3 (2013).

"Dielectric Constant", from the internet, https://macro.Isu.edu/howto/solvents/DielectricConstant.htm; Nov. 19, 2022.

Solvent Polarity Table—Miller's Home, from the internet, https://sites.google.com/site/miller00828/in/solvent-polarity-table; on Nov. 19, 2022.

Thvar, K., "Characterization of the Purity of Curcumin Extraction: Comparative Study of UV Spectrophotometry and High Performance Liquid Chromatography from a Field Application Perspective," *National High School Journal of Science*, Aug. 15, 2012.

Final Office Action from U.S. Appl. No. 17/044,696, dated Nov. 25, 2022.

Non-Final Office Action for U.S. Appl. No. 18/209,360 dated Aug. 1, 2024.

Notice of Allowance from U.S. Appl. No. 17/044,696, Date Mailed: Mar. 15, 2023.

Non-Final Office Action issued in U.S. Appl. No. 18/209,360, dated Oct. 27, 2025.

Final Office Action issued in U.S. Appl. No. 18/209,360 dated Apr. 30, 2026.

* cited by examiner

Placebo 2 Pastille x 3 Times/day
Relative Abundance
80%
70%
60%
50%
40%
30%
20%
10%
0%
26%
25%
71%
69%
Bacteroidetes
Firmicutes
Pre Admin
Post Admin PP composition 2 Pastille x 3 Times/day
Relative Abundance
80%
60%
40%
20%
0%
26%
13%
63%
73%
Bacteroidetes
Firmicutes
Pre Admin
Post Admin PP Comp Substantially Alters F/B Ratio
2.3
129
Change in F/B Ratio
Placebo
PP Composition

*Lim et al Theranostics* 2017; 7(17):4313-4321

A100 = 3x100 mgs AV1016 A200 = 3x200 mgs AV1016

AUC represents the Area Under the Curve of total cytokine levels between 0 and 24 hours N – no cancer, y – yes cancer, a – APG 157, 100 – 100mg, 200 – 200mg TNF-α
A200
P200
A100
P100
AUC (pg.hr/mL)
300
200
100
0
-100
APG-157
Placebo IL-1β
A200
P200
A100
P100
AUC (pg.hr/mL)
15000
10000
5000
0
APG-157
Placebo

| Tissue | Total Reads | DeDuplicated Reads | % Retained | Uniquely Mapped | %Mappability | Mapped To Feature | % Feature Mappability | rRNA | MT-rRNA | %rRNA |
|---|---|---|---|---|---|---|---|---|---|---|
| Post-normal_1 | 1.17E+08 | 6.35E+07 | 54.145 | 5.14E+07 | 80.969 | 3.25E+07 | 63.214 | 1.05E+06 | 1.05E+06 | 0.002 |
| Post-normal_2 | 3.24E+07 | 1.16E+07 | 35.753 | 8.98E+06 | 77.488 | 5.75E+06 | 63.976 | 1.61E+05 | 1.61E+05 | 0.003 |
| Post-tumor_1 | 2.51E+07 | 1.13E+07 | 45.051 | 8.12E+06 | 71.693 | 6.65E+06 | 81.918 | 6.39E+04 | 6.37E+04 | 0.003 |
| Post-tumor_2 | 7.21E+07 | 3.95E+07 | 54.808 | 2.90E+07 | 73.461 | 2.39E+07 | 82.352 | 4.25E+05 | 4.24E+05 | 0.002 |
| Prebiopsy_1 | 2.30E+07 | 7.80E+06 | 33.921 | 5.44E+06 | 69.686 | 4.56E+06 | 83.868 | 2.59E+04 | 2.57E+04 | 0.003 |
| Prebiopsy_2 | 1.75E+07 | 5.42E+06 | 30.902 | 3.72E+06 | 68.561 | 3.11E+06 | 83.754 | 1.73E+04 | 1.71E+04 | 0.008 |

METHODS AND COMPOSITIONS FOR TREATING DYSBIOSIS OF ORAL MICROBIOME

RELATED APPLICATIONS PARAGRAPH

This application is a national stage filing under 35 U.S.C. 371 of International Application No. PCT/US2020/026268, filed Apr. 1, 2020, which claims the benefit of U.S. Provisional Application No. 62/827,645, filed Apr. 1, 2019. The entire teachings of the above application are incorporated herein by reference. International Application No. PCT/US2020/026268 was published under PCT Article 21(2) in English.

BACKGROUND OF THE INVENTION

The human body is the host of a multitude of microbes in anatomical locations including the mouth, esophagus, stomach, small intestine, large intestine, caecum, colon, rectum, vagina, skin, nasal cavities, ears, and lungs. It is well established that the microbiome plays an important role in human health. The microbes, their metabolites, and their interaction with the human host contribute to or participate in a range of biological processes including, but not limited to, development and activity of the immune system, metabolism of food, regeneration of the epithelium, fat storage, production of hormone and vitamins, and protection from pathogens, among others. Any changes in the microbiome from its healthy state (e.g., dysbiosis), which may vary from person to person, can affect human health. More specifically, dysbiosis of the microbiome can lead to initiation, and contribute to the progression of, various diseases. Among the major microbiomes present in the human host—gut, oral and skin microbiomes—oral microbiome is unique in the sense that the dysbiosis of the oral microbiome is believed to be directly or indirectly involved in diseases of the oral cavity, as well as in many systemic diseases. These diseases include a number of infectious diseases, cancers, neurological conditions, metabolic diseases, gastrointestinal conditions, and immunity-related conditions. A number of researchers have demonstrated that the oral microbiome of patients having one of these diseases is different from the microbiome of the healthy population. While a great deal of attention is focused on modulating gut microbiome and impacting the disease conditions, not much effort has been focused on treating the dysbiosis of the oral microbiome. While major phyla of the microbes in the gut and oral microbiome are similar, their relative compositions vary, particularly based on the disease conditions.

Many studies have demonstrated that the dysbiosis of the oral microbiome can point to a population at high risk of developing a particular disease, or the dysbiosis can reflect the existence and/or the progression of a disease. Therefore, a suitable intervention that can modulate the dysbiosis and help restore the homeostasis can help the patients prophylactically, as well as help treat the patients suffering from the disease. Interventions known to modulate the oral microbiota include antibiotics, oral rinses, prebiotics, and probiotics, each of which has limited effects in terms of durability, and at times can lead to significant adverse effects. Also, the durability of the response likely requires potential therapeutic intervention to be administered frequently for extended periods of time, and therefore the therapeutic intervention ought to have an ease of administration, a high level of safety and the manufacturing consistency of a pharmaceutical grade product.

SUMMARY OF THE INVENTION

Disclosed herein are therapeutic compositions and related methods of use. The compositions may induce therapeutically important changes in the microbial population of the oral microbiome from the state of dysbiosis to a state of pre-dysbiosis or homeostasis.

Compositions comprising polyphenols and surfactants may be used in the oral cavity to change the relative population of several phyla (and genera) of microbes in the oral cavity. The effect of changing the relative populations of these groups of microbes (phylum and genus level) is to change the condition from dysbiosis to normal or pre-dysbiosis of the microbiome. Similarly, homeostasis of the oral microbiome is correlated with positive prognosis and/or overall good health.

Disclosed herein are methods of treating or inhibiting a dysbiosis of oral microbiome of a subject. The methods comprise administering a pharmaceutical composition comprising (a) one or more polyphenolic compounds; and (b) an emulsifier or surfactant, thereby treating or inhibiting the dysbiosis of the oral microbiome of the subject.

In some embodiments, the one or more polyphenolic compounds are selected from the group consisting of naturally occurring, synthetic, or semi-synthetic polyphenolic compounds. In some embodiments, the one or more polyphenolic compounds are extracted from one or more plants. In some embodiments, the one or more polyphenolic compounds are derived from the plant *Curcuma longa*. In some embodiments, the one or more polyphenolic compounds are curcuminoids. In some embodiments, the aggregate daily administration of the pharmaceutical composition comprises the one or more polyphenolic compounds in an amount of at least 10 mg.

In some embodiments, the surfactant or emulsifier is selected from the group consisting of a neutral, anionic, cationic, and zwitterionic surfactant and emulsifiers, and combinations thereof. In some embodiments, the pharmaceutical composition further comprises one or more pharmaceutical excipients. In some embodiments, the pharmaceutical composition further comprises one or more food grade excipients.

In some embodiments, the pharmaceutical composition is administered to the subject using a mouthwash, drink, pastille, gummy, troche, solid dispersion, paste, product with oro-mucosal adhesive, spray, oro-mucosal film, or chewing gum. In some embodiments, the administration of the pharmaceutical composition to the subject alters the relative abundance of one or more phyla (e.g., Firmicutes, Bacteroidetes, Proteobacteria, and/or Actinobacteria) in the subject (e.g., in the subject's oral cavity).

In some embodiments, the alteration in the relative abundance of the one or more phyla results in a decrease in the levels of one or more inflammatory cytokines in an oral cavity of the subject. In some embodiments, the one or more inflammatory cytokines are selected from the group consisting of Interleukins (ILs), TNFs, NF-κB, and NF-κB mediated gene products, growth factors, and interferons. In some embodiments, the decrease in the levels of one or more inflammatory cytokines in an oral cavity of the subject results in treating or inhibiting a disease. In some embodiments, the subject has a cancer of the oral cavity, and wherein the decrease in the levels of one or more inflammatory cytokines in the oral cavity of the subject results in treating or inhibiting the cancer. In some embodiments, the subject has a disease not originating in the oral cavity, and wherein the decrease in the levels of one or more inflammatory cytokines in the oral cavity of the subject results in treating or inhibiting the disease.

In some embodiments, the treating or inhibiting the dysbiosis of the oral microbiome of the subject results in treating a disease associated with dysbiosis. In some embodiments, the disease is a precancerous lesion in the oral cavity, leukoplakia or oral squamous cell carcinoma. In some embodiments, the disease is selected from the group consisting of neurological conditions, infectious diseases, cardiovascular diseases, and diseases of the gastrointestinal system.

Also disclosed herein are pharmaceutical compositions. The pharmaceutical compositions comprise (a) one or more polyphenolic compounds; and (b) an emulsifier or surfactant. In some embodiments, the pharmaceutical compositions comprise one or more of the pharmaceutical compositions disclosed in WO 2019/195349, the entire teachings of which are incorporated herein by reference.

In some embodiments, the one or more polyphenolic compounds are selected from the group consisting of naturally occurring, synthetic, or semi-synthetic. In some embodiments, the one or more polyphenolic compounds are extracted from one or more plants. In some embodiments, the one or more polyphenolic compounds are derived from the plant *Curcuma longa*. In some embodiments, the one or more polyphenolic compounds are curcuminoids. In some embodiments, the pharmaceutical composition comprises the one or more polyphenolic compounds in an amount of at least 15 mg.

In some embodiments, the surfactant or emulsifier is selected from the group consisting of a neutral, anionic, cationic, and zwitterionic surfactants and emulsifiers, and combinations thereof. In some embodiments, the pharmaceutical compositions further include one or more pharmaceutical excipients. In some embodiments, the pharmaceutical compositions further include one or more food grade excipients.

In some embodiments, the pharmaceutical composition is administered to a subject to treat or inhibit dysbiosis of an oral microbiome of the subject. In some embodiments, the pharmaceutical composition is formulated for administration to a subject using a mouthwash, drink, pastille, gummy, troche, solid dispersion, paste, product with oro-mucosal adhesive, spray, oro-mucosal film, or chewing gum.

Also disclosed herein are methods of treating or inhibiting a dysbiosis of the oral microbiome of a subject. The methods comprise administering a pharmaceutical composition comprising: (i) one or more polyphenols selected from the group consisting of curcumin, demethoxycurcumin, bisdemethoxycurcumin, tetrahydrocurcumin; and (ii) one or more emulsifiers and/or surfactants.

In some embodiments, the pharmaceutical composition further comprises one or more high polarity compounds isolated from *Curcuma longa* and selected from the group consisting of peptides, polysaccharides, and proteins. In some embodiments, the pharmaceutical composition further comprises one or more non-polar compounds selected from the group consisting of terpenoids, ar-turmerone, α-turmerone, and β-turmerone.

The above discussed, and many other features and attendant advantages of the present invention will become better understood by reference to the following detailed description of the invention when taken in conjunction with the accompanying examples.

BRIEF DESCRIPTION OF THE DRAWINGS

The patent or application file contains at least one drawing executed in color. Copies of this patent or patent application publication with color drawings will be provided by the Office upon request and payment of the necessary fee.

Figures 7A, 7B, 7C, 7D:
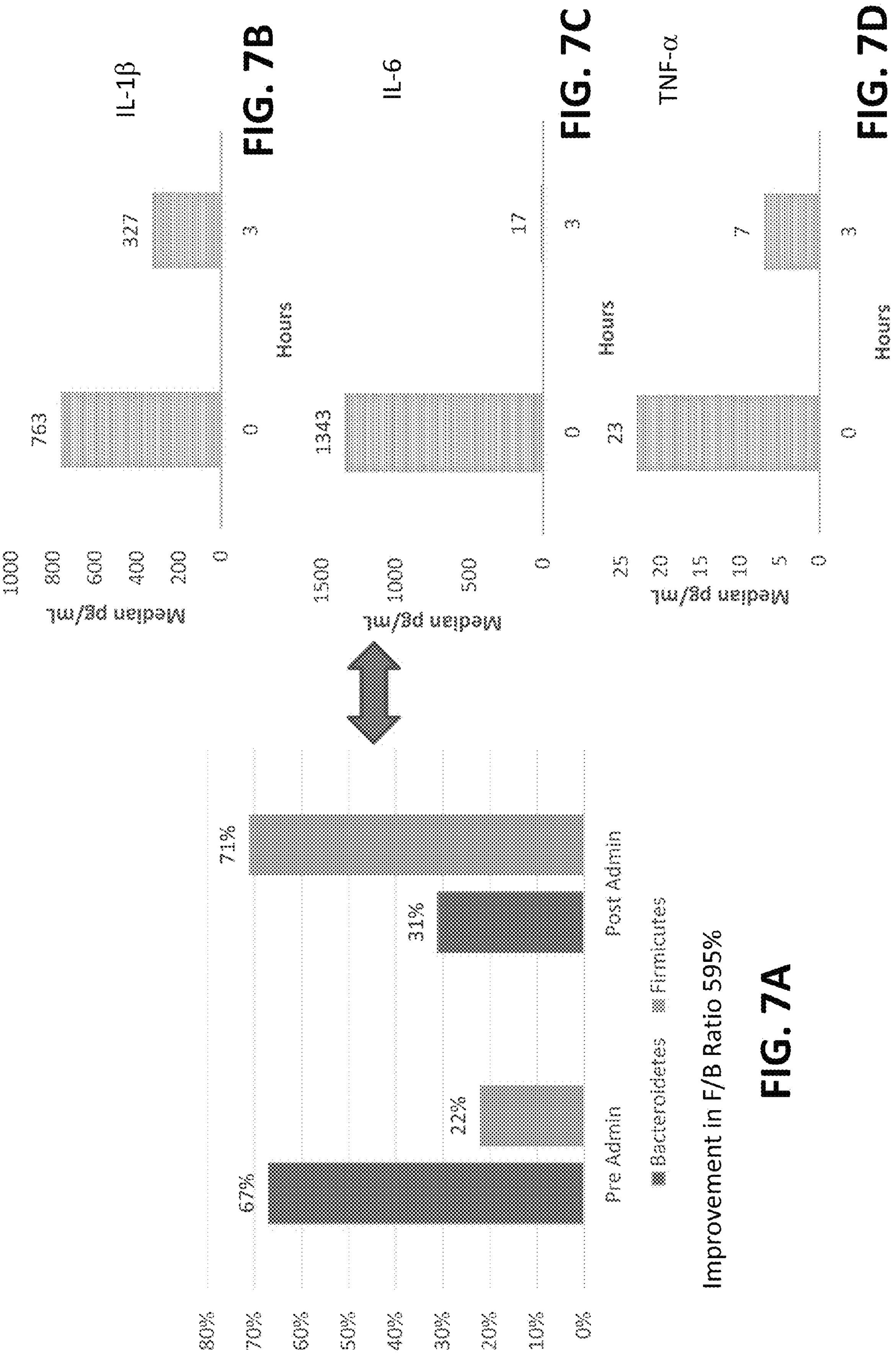
FIGS. 7A-7D demonstrate the effect of a pharmaceutical composition comprising a high polarity extract, a medium polarity extract containing polyphenols, and a low polarity extract combined in a 3:6:1 ratio by weight, respectively, in a hydrogel (AV1016, as disclosed in WO 2019/195349, the entire teachings of which are incorporated herein by reference) on the main phyla of the oral microbiome (FIG. 7A)

and key cytokines (IL-1β (FIG. 7B), IL-6 (FIG. 7C), TNF-α (FIG. 7D)) involved in the pathogenesis of a floor of the mouth oral cancer.

Figure 8:
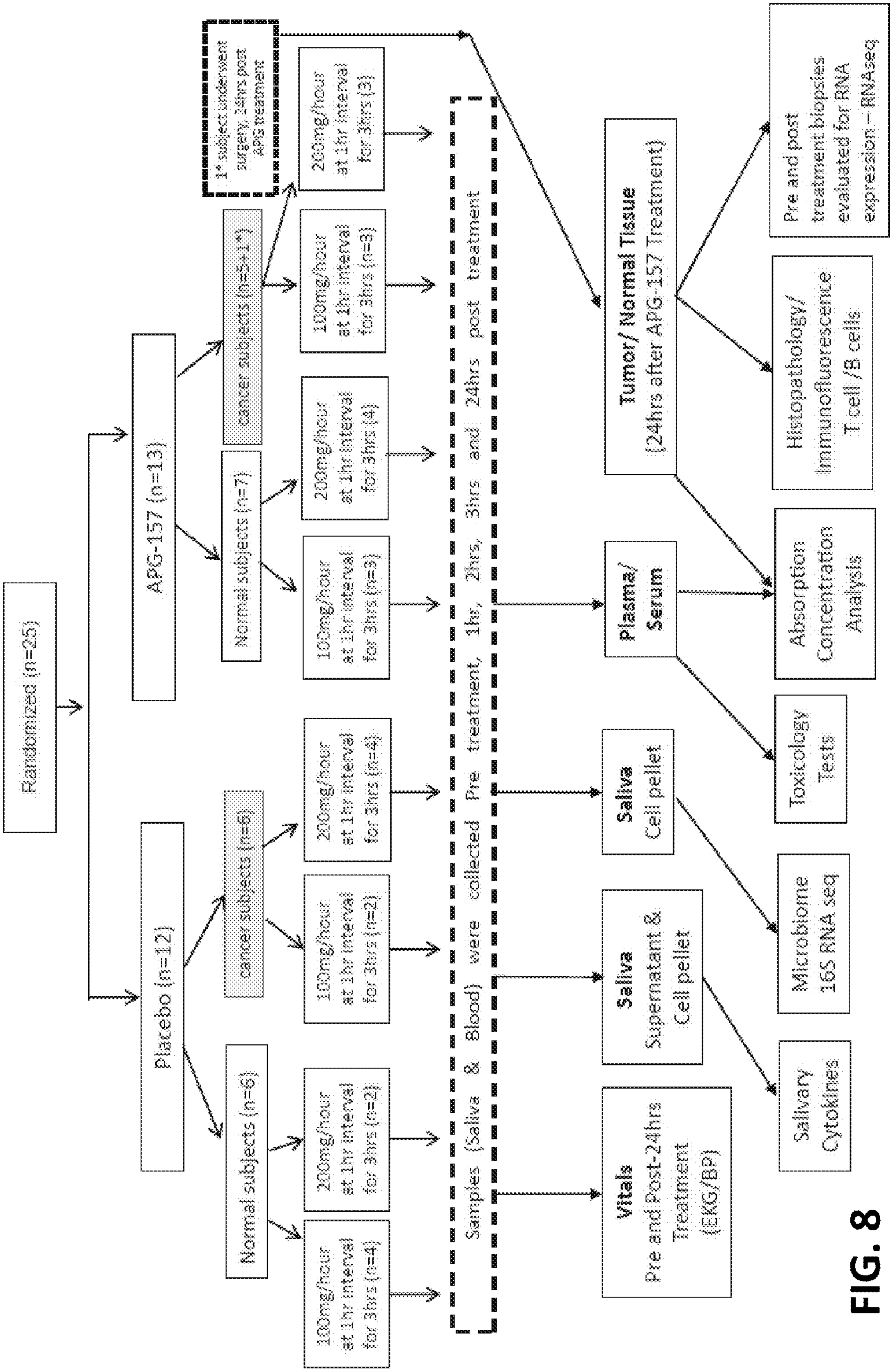

FIG. 8 demonstrate a randomized double-blind, placebo-controlled trial of APG-157 in healthy adult and oral squamous cell carcinoma subjects.

FIGS. 9A-9E demonstrate systemic absorption of curcumin and its analogs in the serum of APG-157 treated subjects. Mixed model with cancer, treatment and time were used as main effects and random batch and subject effects were then fitted in. Time (hours) is included as a class variable in the model. (FIG. 9A) Curcumin (FIG. 9B) sum of all PK variables (FIG. 9C) demethoxycurcumin (DM curcumin) and other curcuminoids (FIG. 9D) and metabolic derivative G curcumin. (FIG. 9E) Combined value pK data of curcumin and analogs demonstrates systemic absorption.

Figure 10B:
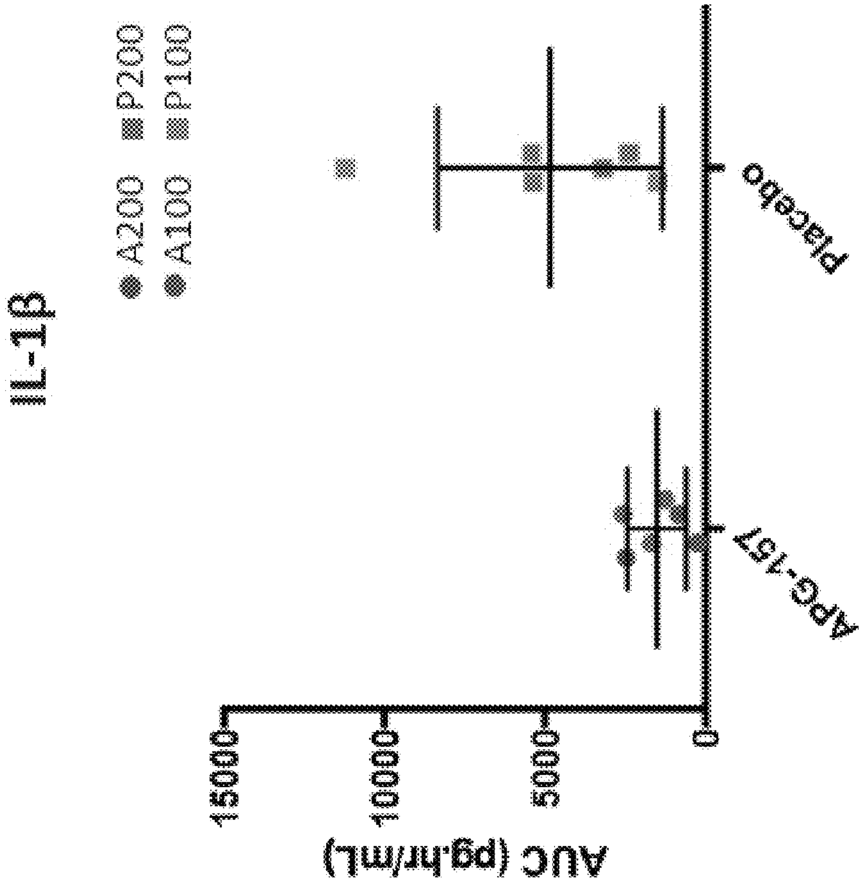
Figure 10A:
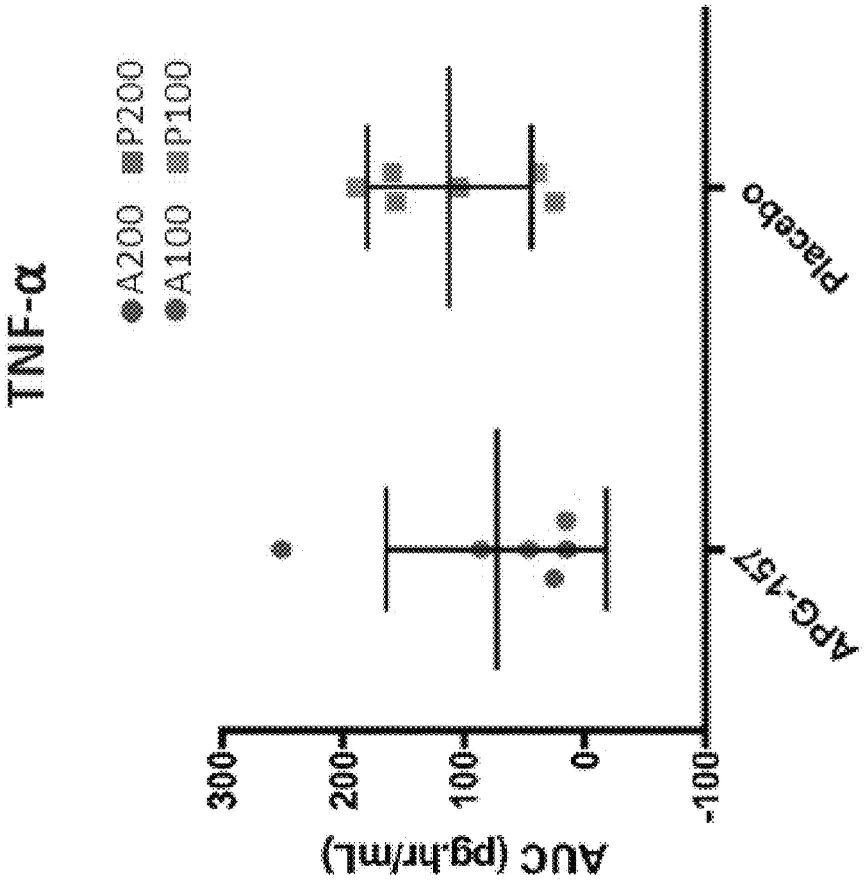
Figure 10C:
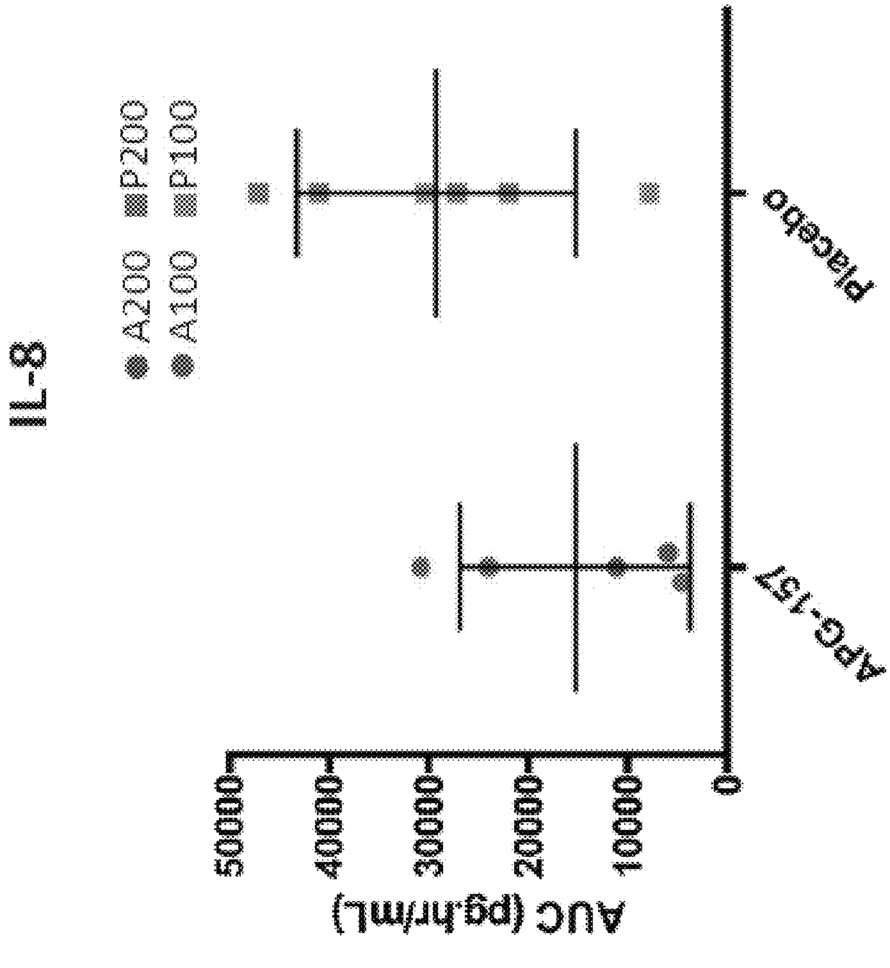

FIGS. 10A-10C demonstrate reduced cytokine levels detected 24 hours post APG-157 treatment in cancer subjects. The area under the curve (AUC) of cytokines (FIG. 10A) TNF-α, (FIG. 10B) IL-1β and (FIG. 10C) IL-8 between 0 and 24 hours points to reduced expression of cytokines in both the 100 mg (A100) and 200 mg (A200) treated salivary supernatant samples.

Figure 11A:
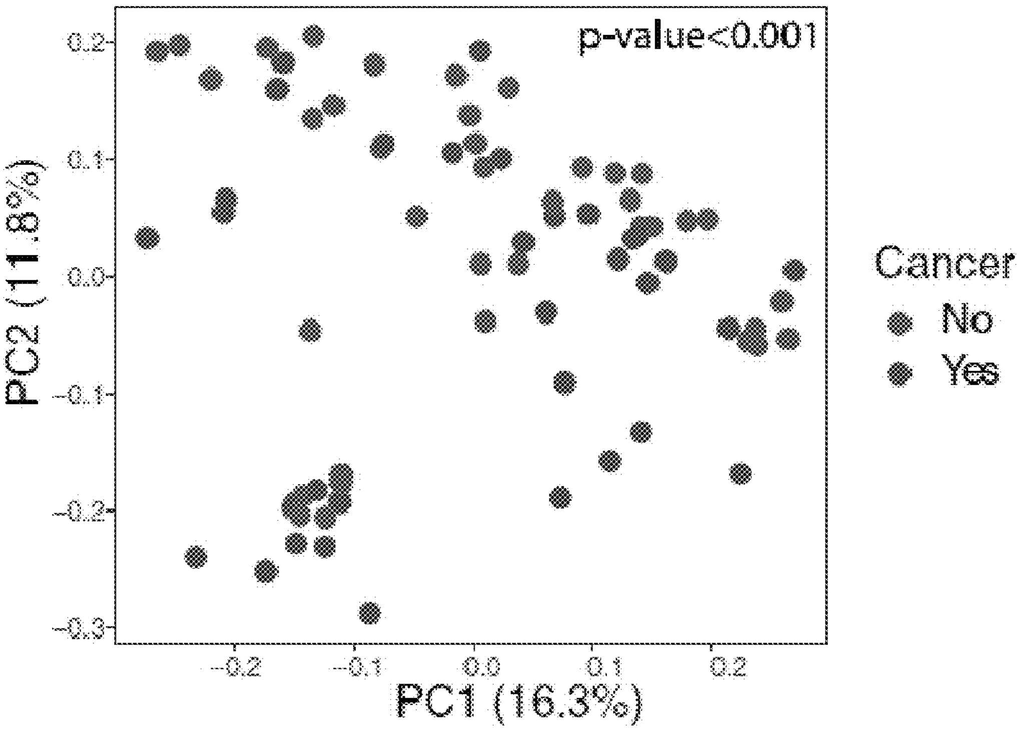
Figure 11B:
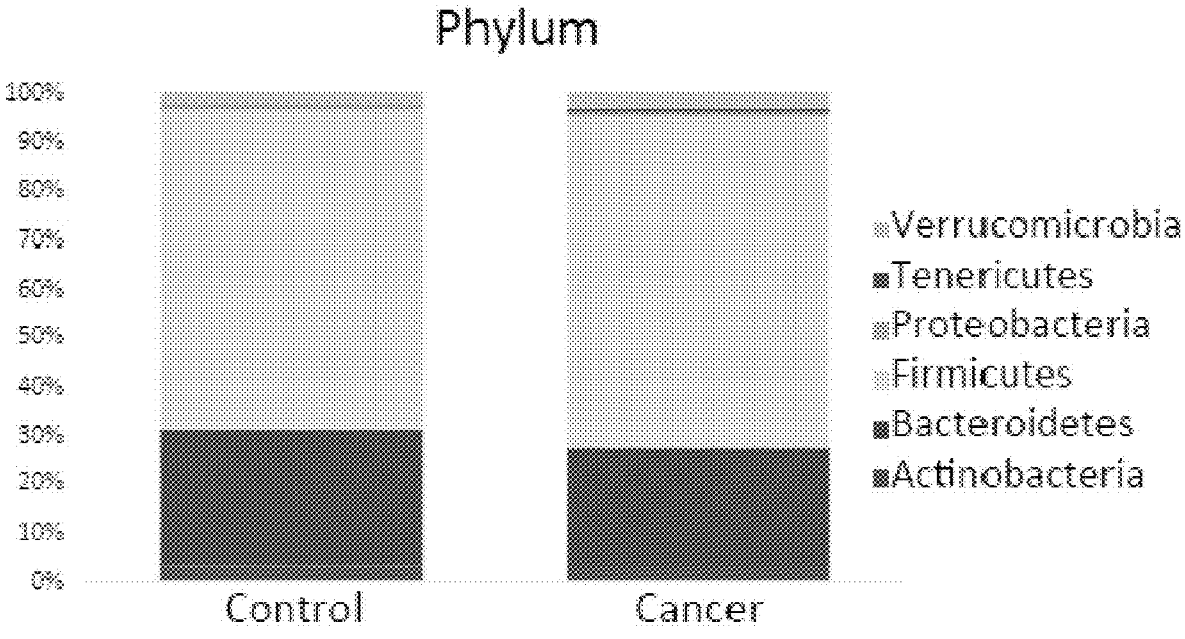
Figure 11B:
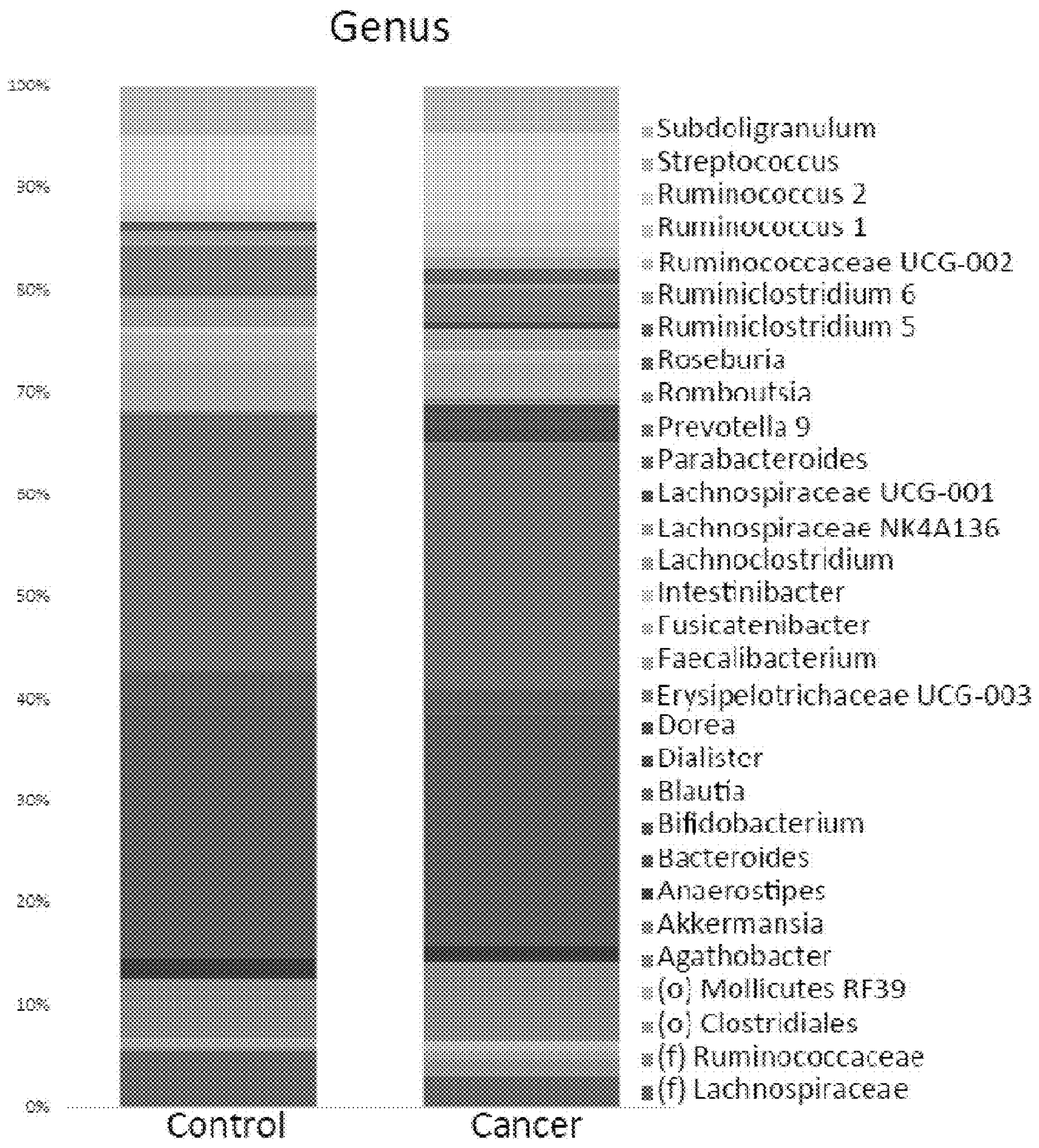
Figure 11C:
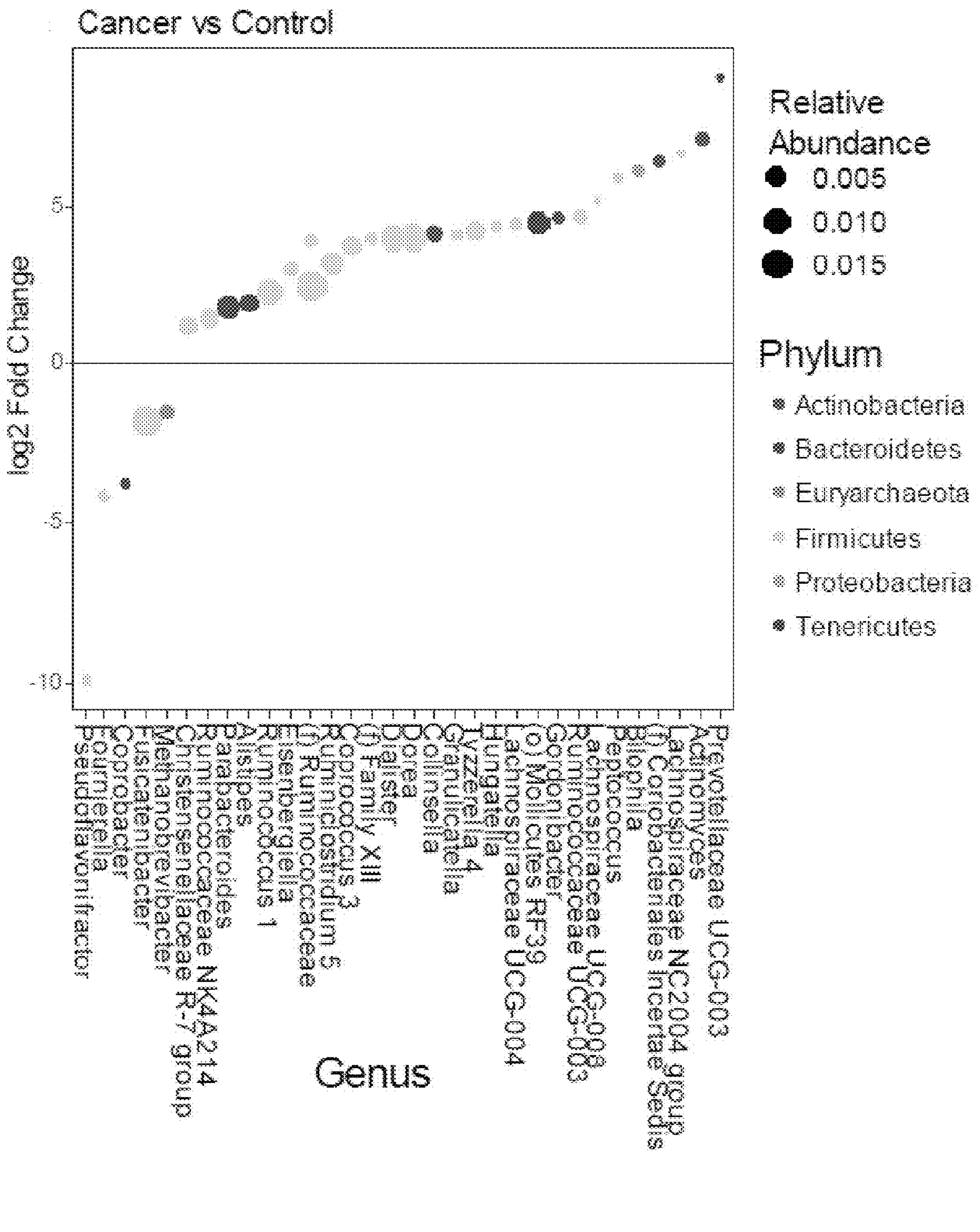

FIGS. 11A-11C demonstrate microbial composition differs in cancer and normal subjects. FIG. 11A provides principal coordinate analysis plot of the cancer versus control subjects with subsequent multivariate P values. FIG. 11B shows taxonomic profiles of control and cancer subjects organized by phylum and genus. FIG. 11C shows differential abundance testing of genera that are statistically different (q value<0.05) between cancer and control subjects. A positive log 2-fold change represents genera that are higher in cancer subjects as compared to control subjects.

Figure 12A:
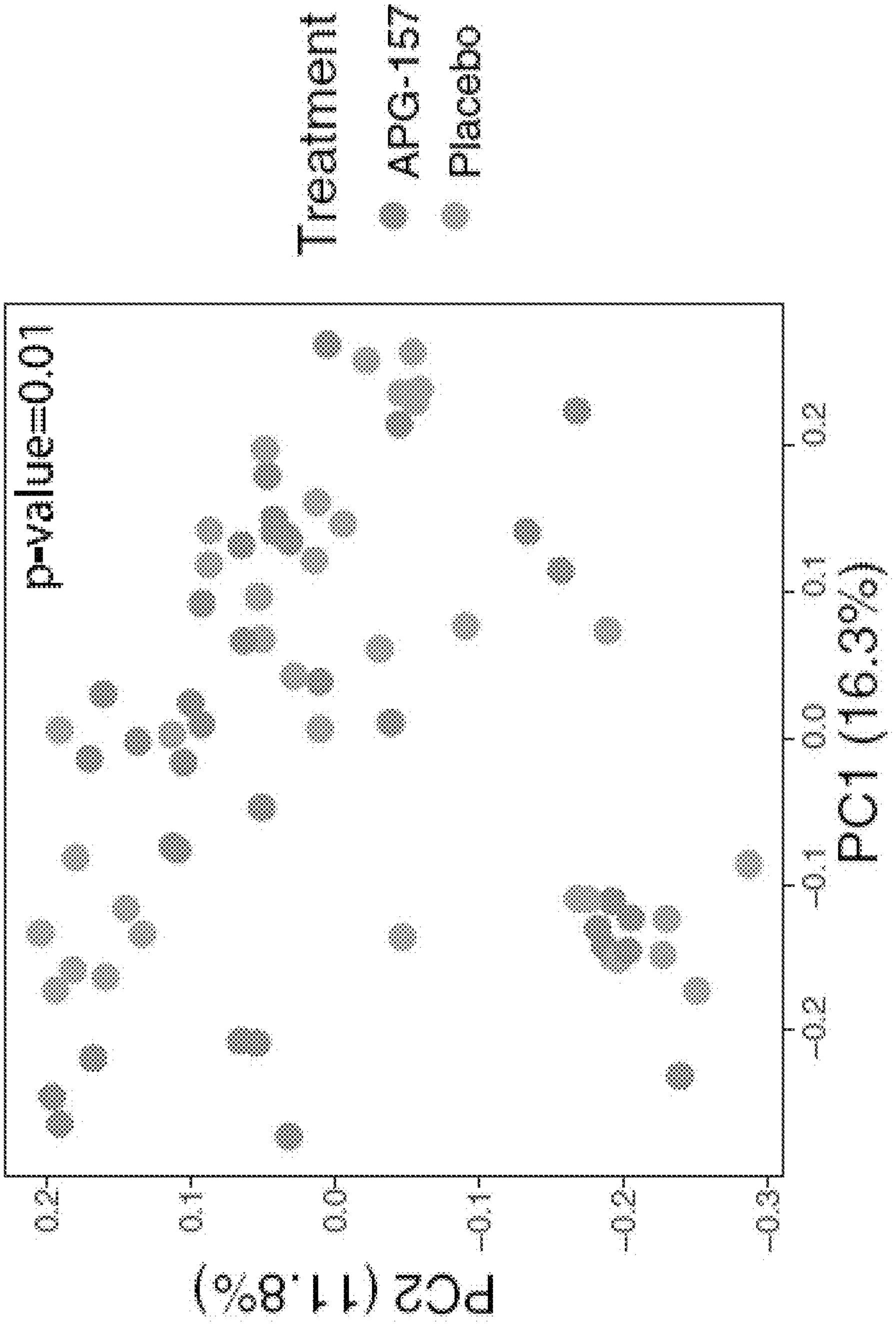
Figure 12B:
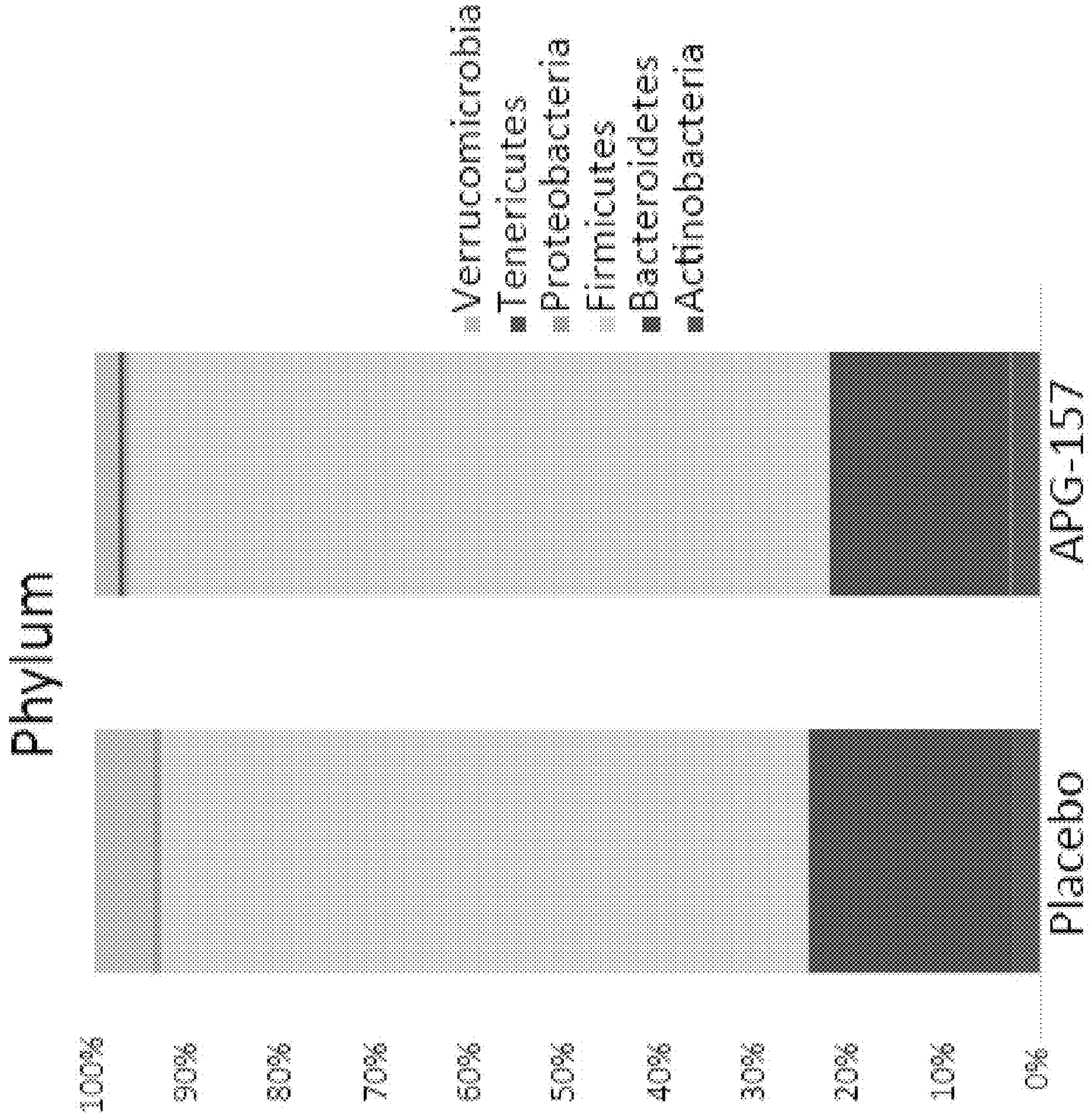
Figure 12B:
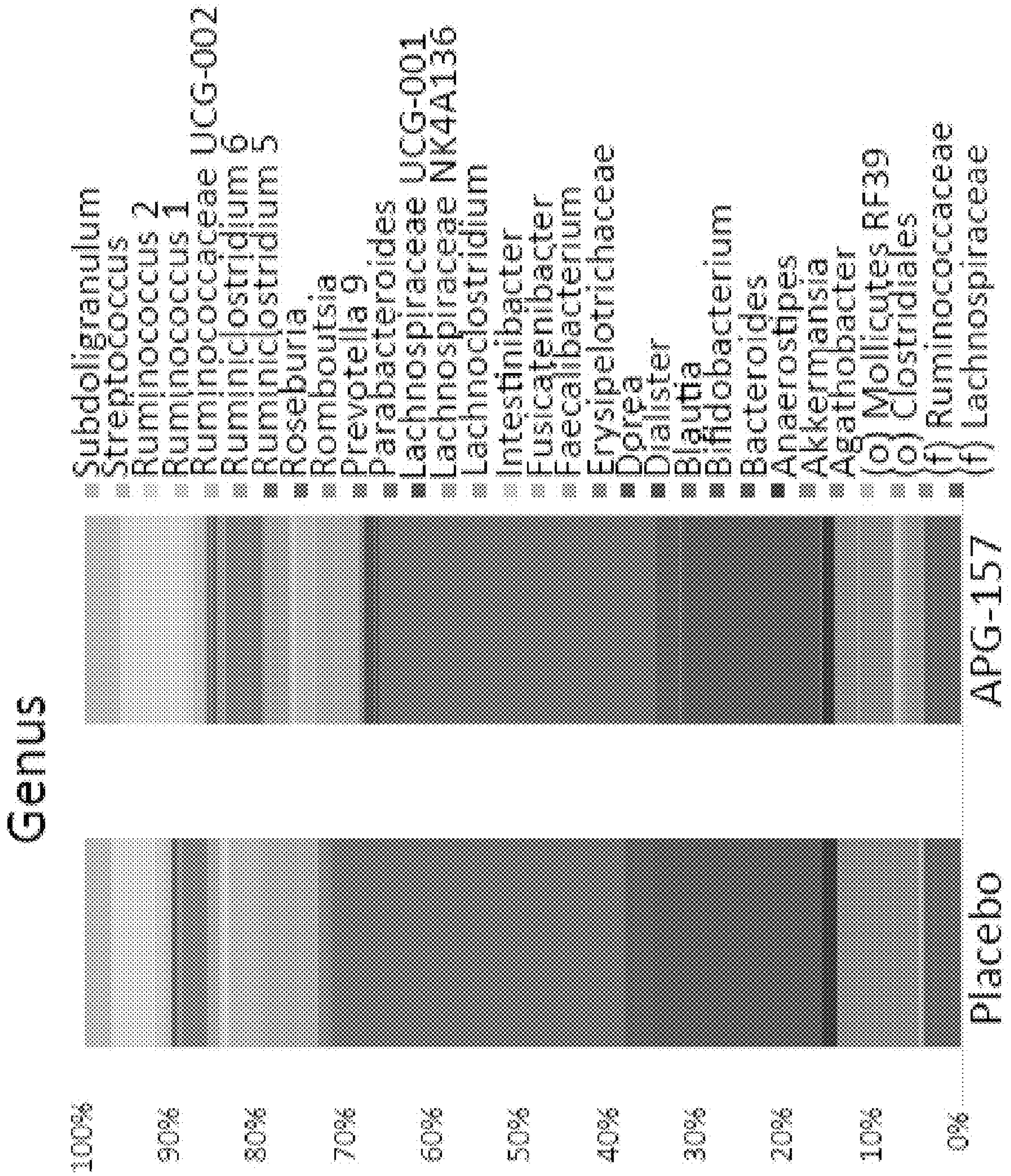
Figure 12C:
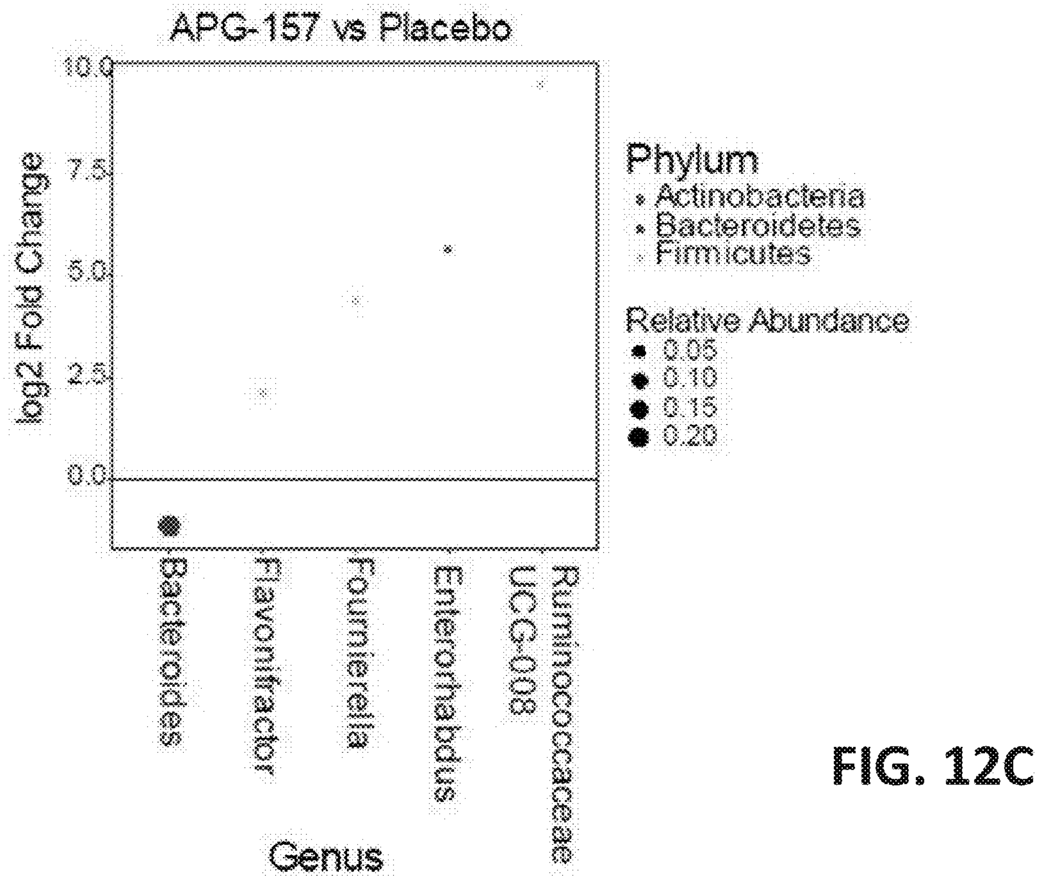
Figure 12D:
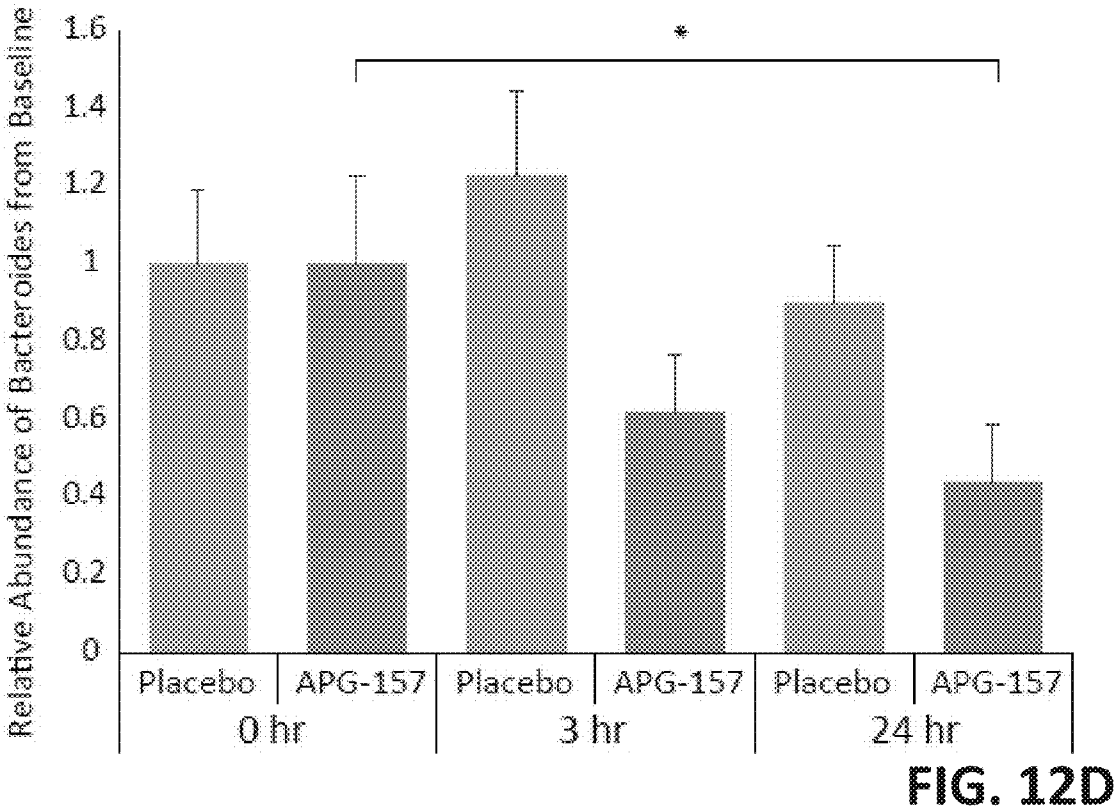

FIGS. 12A-12D demonstrate decrease in *Bacteroides* species in APG-157 treated salivary cells of cancer subjects. FIG. 12A provides principal coordinate analysis plot by treatment with subsequent multivariate P values. FIG. 12B provides taxonomic profiles of placebo versus APG-157 treated cancer subjects organized by phylum and genus. FIG. 12C shows differential abundance testing of genera that are statistically different (q value<0.05) between treatment groups. A positive log 2-fold change represents genera that are higher in APG-157 treated cancer subjects as compared to placebo. FIG. 12D shows representation of relative abundance of *Bacteroides* from baseline of cancer subjects treated with placebo versus APG-157 shows decrease in *Bacteroides* species in APG-157 treated salivary cells of cancer subjects.

Figures 13A, 13B:
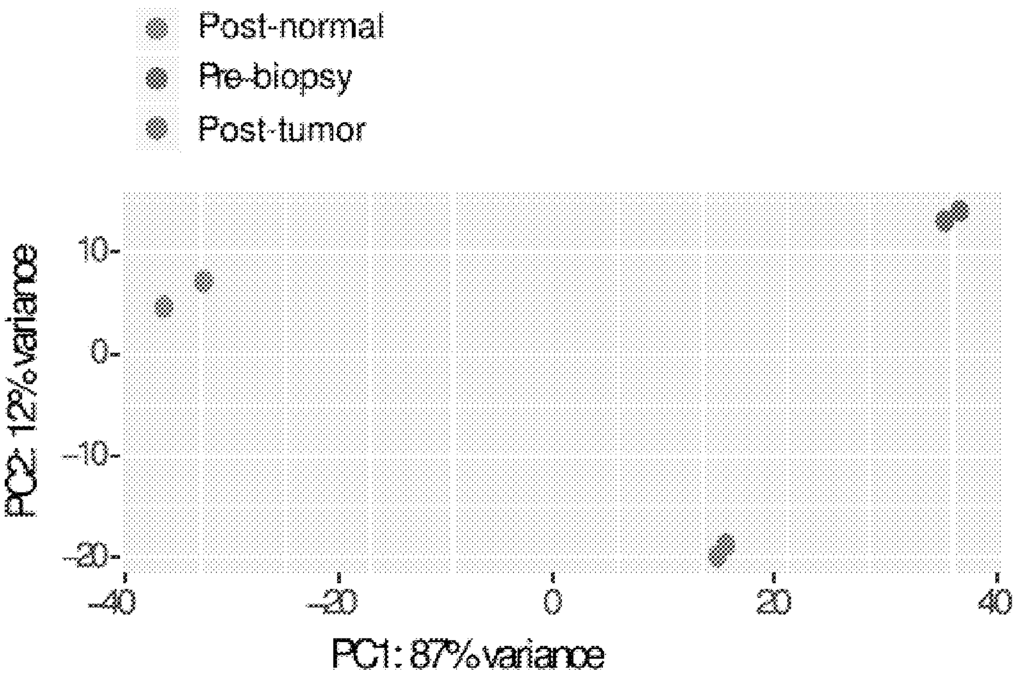
Figure 13C:
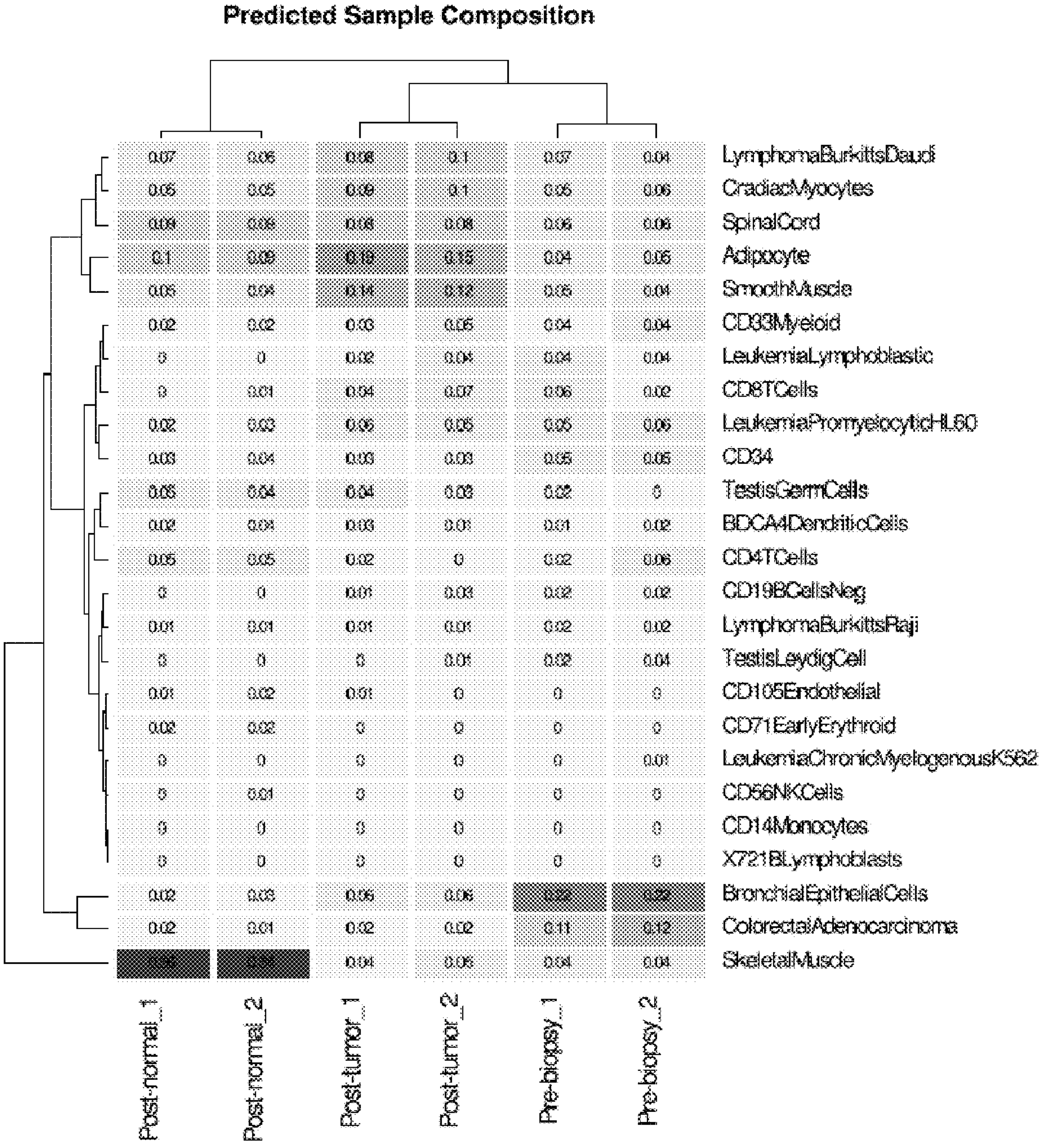

FIGS. 13A-13C demonstrate differential tissue specific expression in pre and post treatment tissue samples. FIG. 13A provides a table with RNAseq statistics of FFPE samples points to the number of reads in each sample. FIG. 13B shows unsupervised clustering of FFPE RNAseq samples and PCA plot showing the percentage of variance explained by the first two principal components. All genes with normalized counts higher than 1 for all samples were used in this analysis. Gene counts were transformed using variance-stabilization. FIG. 13C shows GEDIT tissue deconvolution output, using all tissues as reference.

Figure 14A:
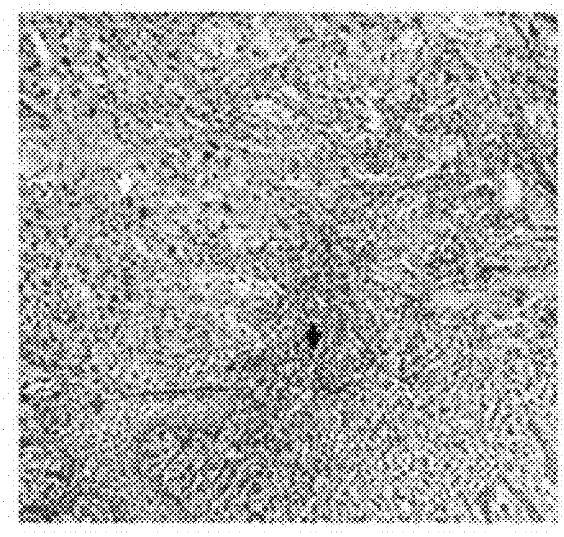
Figure 14B:
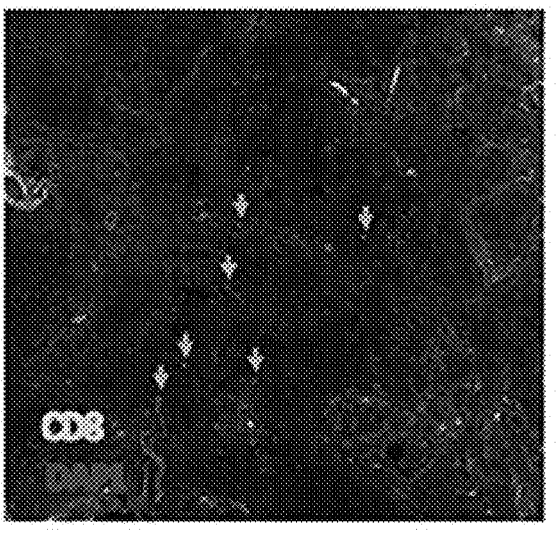
Figure 14C:
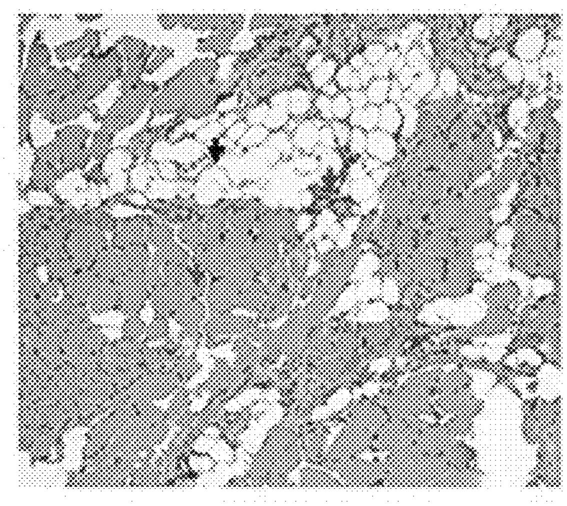
Figure 14D:
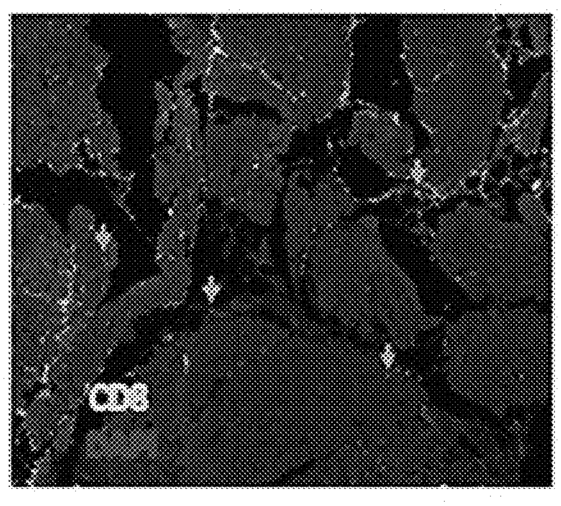
Figure 14E:
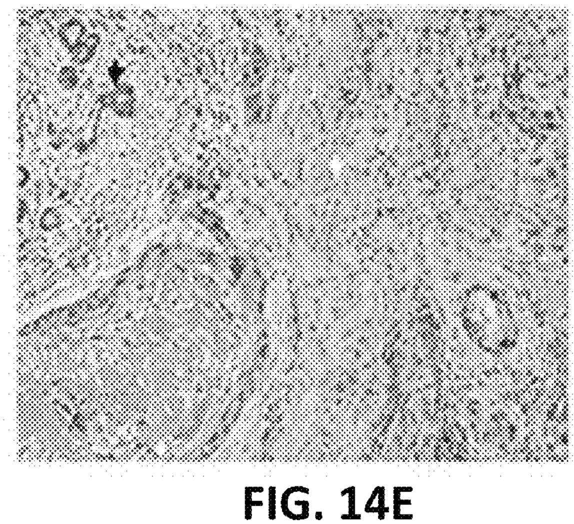
Figure 14F:
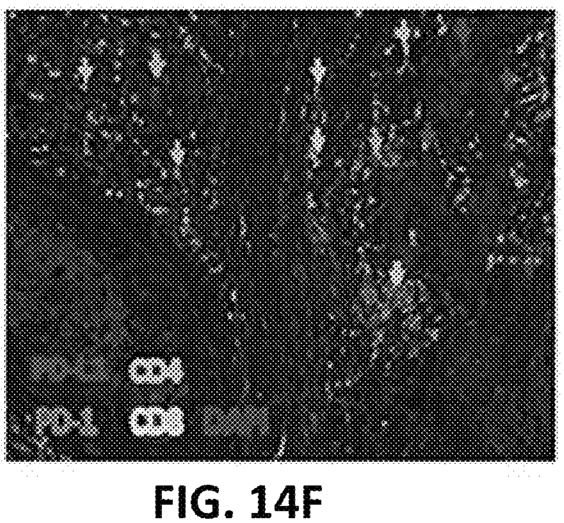
Figure 14G:
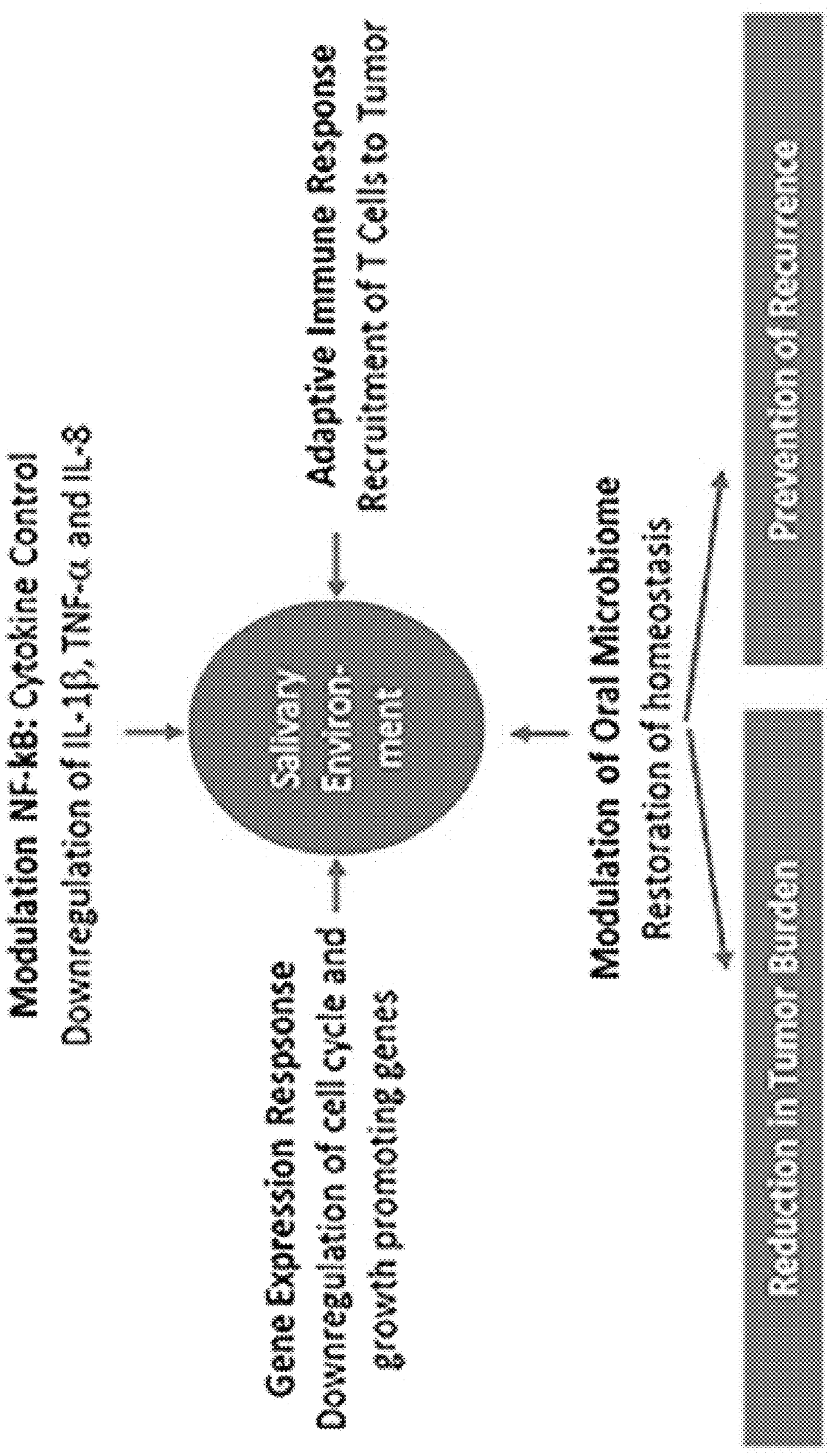

FIGS. 14A-14G demonstrate expression of CD4 and CD8 positive T cells in the post APG-157 treated tumor tissue. FIGS. 14A and 14C show H & E staining shows the presence of adipocytes (black arrows), skeletal muscle (green arrows), nerve cells (white arrows) and lymphocytes (red arrows) in the pre-biopsy and post treated normal tissues. FIG. 14B shows scattered CD8 positive T cells (cyan arrows) are seen in the pre-biopsy tumor cells and CD4 positive T cells are absent in these cells. FIG. 14D show scattered CD8 positive T cells and absence of CD4, PD-1 and PD-L1 expressing cells are seen in the normal tissue sample. FIG. 14E show H & E staining of the post treated tumor tissue shows the presence of salivary gland, tumor cells and fibrous stroma represented by black, green and white arrows respectively. FIG. 14F show PD-L1 (red arrows), PD-1 (green arrows), CD8 (cyan arrows), and CD4 (orange arrows) positive cells points to the expression of PD-L1 in response to T cell infiltration into the tumor microenvironment called, 'adaptive PD-L1 expression' suggesting that immune checkpoint blockade (anti-PD-1 or anti-PD-L1 antibody) could work under these conditions. FIG. 14G provides a model of APG-157 mediated effect points to the inhibitory role of curcumin and its analogs on multiple cell signaling pathways.

DETAILED DESCRIPTION OF THE INVENTION

Disclosed herein are compositions and methods for treating the dysbiosis of the oral microbiome. The compositions may comprise a combination of phenolic molecules and surfactants and/or emulsifiers that may be delivered orally.

In some embodiments, a polyphenol is any compound that contains more than one phenolic moiety. A polyphenol may be a natural compound or may be a semi or fully synthetically made compound. In certain aspects the polyphenol is a natural compound. In some aspects a polyphenol is selected from the group consisting of stilbenes (e.g., resveratrol), flavonoids, lignans, and phenolic acids. In certain embodiments a polyphenol is (1E,6E)-1,7-bis(4-hydroxy-3-methoxyphenyl)-1,6-heptadiene-3,5-dione. Non-limiting examples of various polyphenol compounds include the following:

Structures of Curcumin, ECGC, Quercetin and Resveratrol

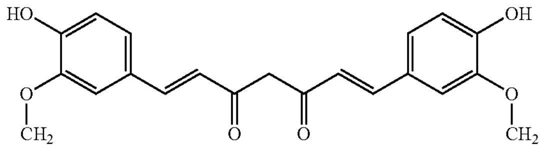

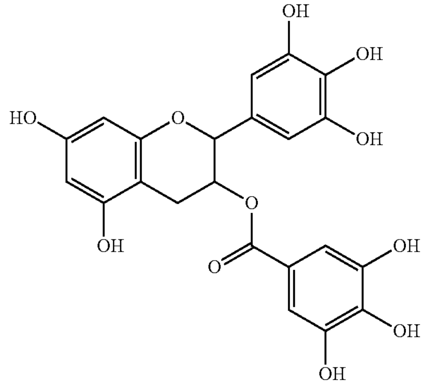

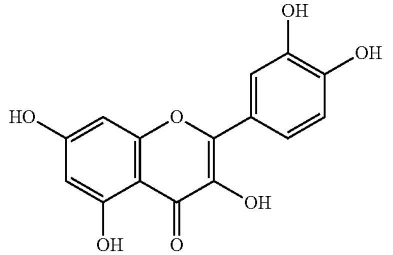

-continued

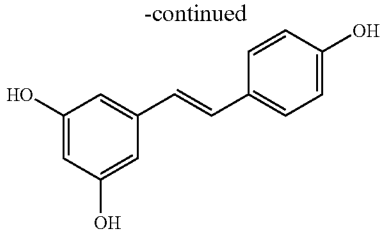

In some embodiments, a surfactant or emulsifier is any naturally occurring compound or is a synthetically made, food or pharmaceutical grade compound. A surfactant may be a nonionic surfactant, a cationic surfactant, an anionic surfactant, a zwitterionic surfactant or combinations thereof. Examples of an FDA approved surfactant include, but are not limited to, cetearyl alcohol, cetyl alcohol, cholesterol, glyceryl oleate, glyceryl stearate, glyceryl palmitostearate, lanolin, poloxamers, polyoxyethylene alkyl ethers, polyoxyl castor oil, polysorbates, polyoxyl stearates, sorbitan esters, sucrose esters, cetrimide, cetylpyridinium chloride, docusate sodium, oleic acid, sodium lauryl sulfate, stearic acid, and lecithin.

In some embodiments, the composition is formulated for administration to a subject. In some aspects the composition is formulated for oral administration, buccal administration, and/or sublingual administration to a subject. Additional modes of administration of a pharmaceutical composition are described herein and are known by those of skill in the art. In some aspects the pharmaceutical composition is administered to a subject using any method of delivery that ensures sufficient residence time in the oral cavity. In some aspects the pharmaceutical composition is administered to a subject using a mouthwash, drink, pastille, gummy, troche, solid dispersion, paste, product with oro-mucosal adhesive, spray, oro-mucosal film, or chewing gum.

In some embodiments, the pharmaceutical composition comprises one or more pharmaceutical or food grade excipients. In some aspects the one or more pharmaceutical excipients are selected from the group consisting of diluents, disintegrants, carriers (e.g., hydrogel matrix), binders, adhesives, surfactants, lubricants, solvents, permeation enhancers (e.g., menthol, surfactants, alcohols, polyols, polyethers, cyclodextrin, and fatty acid derivatives), plasticizers, gelling agents, water, release agents, flavorings, sweeteners, preservatives, and combinations thereof. In certain aspects the one or more pharmaceutical excipients are selected from the group consisting of glycerin, gelatin, water, saline, dextrose, glycerol, ethanol, and combinations thereof. Additional pharmaceutical excipients are described herein and are known by those of skill in the art.

A pharmaceutical composition described herein comprises a polyphenol and a surfactant and/or emulsifier. In some embodiments the pharmaceutical composition comprises one or more extracts of *Curcuma longa*, as described herein. In certain aspects the pharmaceutical composition comprises (a) one or more extracts of *Curcuma longa* enriched with: (i) one or more high polarity compounds selected from the group consisting of peptides, polysaccharides, and proteins; (ii) one or more medium polarity compounds selected from the group consisting of polyphenols, curcumin, demethoxycurcumin, and bisdemethoxycurcumin; and (iii) one or more non-polar compounds selected from the group consisting of terpenoids, ar-turmerone, α-tumerone, and β-turmerone; and (b) one or more pharmaceutical excipients. Examples of such pharmaceutical compositions are described in WO 2019/195349, incorporated herein by reference in its entirety.

In some embodiments the pharmaceutical composition comprises (i) one or more polyphenols selected from the group consisting of curcumin, demethoxycurcumin, bisdemethoxy curcumin and tetrahydrocurcumin; and (ii) one or more emulsifiers and/or surfactants. In some aspects the pharmaceutical composition is supplemented with one or more high polarity compounds isolated from *Curcuma longa* and selected from the group consisting of peptides, polysaccharides, and proteins; and/or one or more non-polar compounds selected from the group consisting of terpenoids, ar-turmerone, α-turmerone, and β-turmerone.

In some aspects the polyphenol compound determines the amount of surfactant and/or emulsifier needed to create a therapeutic product. For example, a sufficient amount of surfactant and/or emulsifier is required to ensure the polyphenol is delivered in an effective manner (e.g., controlled continuous or frequent release over time) to achieve extended effective contact with the oral microbial environment. In some aspects the pharmaceutical composition comprises at least 5 mgs, at least 10 mgs, at least 15 mgs, at least 20 mgs, or at least 25 mgs of polyphenol, and in certain aspects comprises at least 15 mgs of polyphenol. In some aspects the pharmaceutical composition comprises emulsifier and/or surfactant in an amount of at least 0.5%, at least 1.0%, at least 1.5%, or at least 2% of the corresponding polyphenol amount.

The oral microbiome may play a significant role in the initiation and progression of one or more diseases. For example, dysbiosis of the oral microbiome may be directly or indirectly involved in diseases of the oral cavity, as well as in many systemic diseases. In some aspects the oral microbiome plays a role in one or more infectious diseases, cancers, neurological conditions, metabolic diseases, gastrointestinal conditions, and/or immunity-related conditions. In some aspects administration of the pharmaceutical composition to a subject results in treating or inhibiting one or more diseases associated with dysbiosis of the oral microbiome. In certain aspects administration of the pharmaceutical composition to a subject results in treating or inhibiting leukoplakia or oral squamous cell carcinoma. In certain aspects administration of the pharmaceutical composition to a subject results in treating or inhibiting neurological conditions, infectious diseases, cardiovascular diseases, and/or diseases of the gastrointestinal system.

In some embodiments the pharmaceutical composition comprising one or more polyphenols, and one or more emulsifiers and/or surfactants is administered to a subject to treat the dysbiosis of the gut microbiome. In some aspects the treatment of the dysbiosis of the oral microbiome in a subject results in treating the dysbiosis of the gut microbiome of the subject.

In some embodiments, microbiome modulation involves modulating the relative ratios of different phyla, where each phylum comprises various genera of microbes. In some aspects dysbiosis of the oral microbiome results in an increase in the relative abundance of Bacteroidetes and a decrease in the relative abundance of Firmicutes. In some aspects the pharmaceutical composition comprising a polyphenol and a surfactant/emulsifier, upon administration to a subject, increases the relative abundance of Firmicutes and reduces the relative abundance of Bacteroidetes in the oral microbiome. In some aspects the relative ratios of other phyla (e.g., Firmicutes, Bacteroidetes, Proteobacteria, Actinobacteria, etc.) may be modulated depending on the disease.

In some aspects modulating the relative ratios of different phyla (e.g., changing the relative abundance of phyla) results in a decrease in the levels of one or more inflammatory cytokines. In some aspects modulating the relative ratios of different phyla (e.g., changing the relative abundance of phyla) results in an improvement in the cytokine profile of the saliva of a subject (e.g., returning the cytokine profile to homeostasis levels). The one or more inflammatory cytokines may be selected from the group consisting of Interleukins (ILs), TNFs, NFκB, and NF-κB mediated gene products, growth factors, and interferons. In some aspects the levels of one or more inflammatory cytokines are decreased in the oral cavity of a subject. Abnormal levels (e.g., high levels) of inflammatory cytokines may be present in the oral cavity of a subject when the subject has a disease or condition. In some aspects the subject has a disease of the oral cavity (e.g., a cancer or a precancerous lesion within the oral cavity). In some aspects the subject has a disease that does not originate in the oral cavity. In some embodiments decreasing the levels of one or more inflammatory cytokines in the oral cavity of a subject results in treating or inhibiting a cancer located within the oral cavity of the subject.

Also disclosed herein are compositions and related methods of use or manufacture of poly-pharmaceutical drugs that consist of combinations of different compounds isolated from *Curcuma longa*. For example, in some aspects, a poly-pharmaceutical drug consists of one or more polyphenols in combinations with one or more compounds isolated from *Curcuma longa* (e.g., one or more high polarity compounds selected from the group consisting of peptides, polysaccharides, and proteins and/or one or more non-polar compounds selected from the group consisting of terpenoids, ar-turmerone, α-turmerone, and β-turmerone).

In certain embodiments, the inventions disclosed herein concern a two-step process of preparing the compositions disclosed herein. In the first step, the selective enrichment and/or depletion of various classes of compounds present in *C. longa* using various methods of extraction takes place. These extraction processes are based on the use of solvent systems of varying polarity. For example, a low or non-polar extract is obtained by extracting the botanical material using a solvent system that has a dielectric constant of less than 5, or a relative polarity of less than 0.2. A medium polarity extract (e.g., that contains polyphenols) is obtained by extracting the botanical material using a solvent system that has a dielectric constant between 5 and 25, or the relative polarity between 0.25 and 0.6. A high polarity extract is obtained using a solvent system that has a dielectric constant greater than 25, or a relative polarity greater than 0.6. In the second step, these extracts are combined to create an optimized formulation based on the in-vitro and in-vivo evaluation, thereby creating an artificial ratio of the polyphenols to other compounds that is unique relative to the ratios of such compounds that occur naturally in the plant.

The pharmaceutical composition may further include one or more pharmaceutical excipients. The pharmaceutical excipient may be selected from the group consisting of plasticizer, gelling agent, water, release agent, flavoring, sweetener, preservative, diluents, disintegrants, carriers (e.g., a hydrogel matrix), binders, adhesives, surfactants, lubricants, solvents, permeation enhancers (e.g., menthol, surfactants, alcohols, polyols, polyethers, cyclodextrin, fatty acid derivatives), and mixtures thereof. Suitable excipients may include, for example, glycerin, gelatin, water, saline, dextrose, glycerol, ethanol or the like, and combinations thereof. In certain aspects, the compositions disclosed herein may comprise one or more of the pharmaceutical excipients disclosed in U.S. Pat. No. 9,913,873, the entire contents of which are incorporated by reference herein.

Also disclosed herein are methods of treating diseases or conditions in a subject associated with a dysbiosis of the oral microbiome comprising administering the compositions disclosed herein to the subject. In some aspects the disease or condition is cancer. In some aspects the disease or condition is a precancerous lesion. In some aspects the disease or condition is leukoplakia. In some embodiments, a method of treating cancer includes administering to the subject in need thereof an effective amount of the pharmaceutical composition described herein, thereby treating cancer. In some aspects, cancer is oral cancer (e.g., oral squamous cell carcinoma). In some aspects, cancer is Gliobastoma, lung cancer, colon cancer, or pancreatic cancer.

As used herein, a "subject" means a human or animal (e.g., a primate). Usually, the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. In addition, the methods described herein can be used to treat domesticated animals and/or pets. A subject can be male or female. A subject can be one who has been previously diagnosed with or identified as suffering from or having a condition in need of treatment or one or more complications related to such a condition, and optionally, but need not have already undergone treatment for a condition or one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

An effective amount of the pharmaceutical composition administered to a subject comprises at least about 10 mgs to 600 mgs per dose, and in some aspects at least about 200-500 mg per day of the active ingredients. This amount comprises the polyphenol combined with a surfactant and/or emulsifier.

In some embodiments, the pharmaceutical composition is formulated for administration to a subject (e.g., oral, buccal, transdermal or sublingual administration). Pharmaceutical compositions comprise one or more agents or compositions that have therapeutic utility, and a pharmaceutically acceptable carrier (e.g., a carrier that facilitates delivery of agents or compositions). Exemplary methods for administering the pharmaceutical composition to the subject include oral, buccal, sublingual and/or transdermal administration.

The pharmaceutical compositions described herein may be delivered to a subject by means of a pharmaceutically acceptable carrier. Such carriers are well known in the art and can be one or more compatible solid or liquid vehicles, fillers, diluents, or encapsulating substances which are suitable for administration to a human or non-human animal. In preferred embodiments, a pharmaceutically acceptable carrier is a non-toxic material that does not interfere with the effectiveness of the biological activity of the active ingredients. The term "compatible," as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically acceptable carriers should be of sufficiently high purity and sufficiently low toxicity to render them suitable for administration to the human or non-human animal being treated.

Some examples of substances which can serve as pharmaceutically acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; fish oil such as those containing long-chain omega-3 polyunsaturated fatty acids (PUFA); polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

Pharmaceutically acceptable compositions can include diluents, fillers, salts, buffers, stabilizers, solubilizers and other materials which are well-known in the art. The choice of pharmaceutically acceptable carrier to be used in conjunction with the compounds of the present invention takes into consideration the way the compound is to be administered to the subject. Such preparations may routinely contain one or more salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof in certain embodiments. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts. It will also be understood that a compound can be provided as a pharmaceutically acceptable pro-drug, or an active metabolite can be used.

The pharmaceutical composition may be administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be formulated into preparations in solid, semi-solid, liquid or gaseous forms such as tablets, capsules, powders, granules, ointments, solutions, depositories, inhalants, and usual ways for oral administration. The invention also embraces pharmaceutical compositions which are formulated for local administration, such as by implants. In some aspects the pharmaceutical composition is formulated for administration as a pastille. Examples include those described by U.S. Pat. No. 9,913,873, incorporated herein by reference.

Compositions suitable for oral administration may be presented as discrete units, such as capsules, tablets, lozenges, each containing a predetermined amount of the active agent. Other compositions include suspensions in aqueous liquids or non-aqueous liquids, such as syrups, elixirs and/or emulsions.

In some embodiments, the pharmaceutical composition is administered in combination with one or more therapies. Therapies may be selected from the group consisting of immunotherapy, chemotherapy, radiotherapy, proton therapy, surgery, and combinations thereof. The composition may be administered before, during, or after administration of a therapy. In some aspects, the composition is administered in combination with one or more chemotherapeutic agents. The pharmaceutical compositions described herein may further include one or more chemotherapeutic agents.

The chemotherapeutic agent may be an antineoplastic agent. In some aspects, the antineoplastic agents are selected from the group consisting of antimetabolite agents, antibiotic-type agents, alkylating agents, hormonal agents, immunological agents, interferon-type agents, matrix metalloproteinases, and superoxide dismutase mimics.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity, those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Plants, mammals and microbes co-evolved over millennia and thus both plants and humans have been the hosts to a vast community of microbes. Reciprocal relationships between plants and microbes and mammals and the microbes have been conserved through the evolution. Indeed, comparisons between bacterial communities associated with the rhizosphere and the mammals' gut-both functionally responsible for absorption of nutrients-show that both ecosystems are dominated by the same four bacterial phyla (Firmicutes, Bacteroidetes, Proteobacteria, Actinobacteria), albeit in different relative abundances.

Plants interact with microbes through the metabolites they produce. One of the major classes of the plant metabolites are polyphenols. The polyphenols have been known to affect the human gut microbiome in a beneficial manner. In order to use polyphenol-based interventions for modulating the oral microbiome, it is necessary to create the means by which the oral microbiome is exposed to or in contact with polyphenolic compounds.

Polyphenolic compounds are usually lipophilic in nature and therefore do not mix well with saliva, the main body fluid that is in contact with the oral microbiome. If a sufficient amount of polyphenol is not taken up by the saliva, most of the polyphenols will travel down the gastrointestinal tract along with the swallowed saliva. Therefore, in order to increase the residence time of the polyphenols in the saliva, it is important to deliver the polyphenols in a formulation whereby polyphenols can be miscible with the saliva. An average, normal volume of saliva is about 1 mL. Therefore, it is also important that unusually large amounts of polyphenols are not discharged bolus into the saliva, overwhelming its ability to retain the polyphenols. A preferred method of delivering the polyphenol is a controlled, continuous or frequent release over time to achieve extended effective contact with the oral microbial environment. The present inventors have, therefore, developed formulations whereby polyphenol and an appropriate emulsifier and/or surfactant are combined to make a therapeutic product that can be administered to a subject.

Modulating the Oral Microbiome with a Composition Containing Polyphenols

Figure 1A:
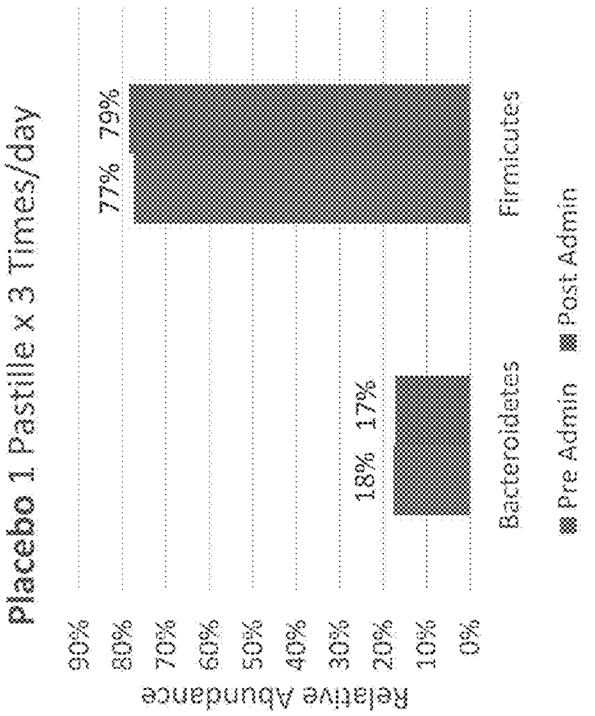
FIGS. 1A-1C demonstrate the effect of a polyphenolic (PP) compound on the relative population of the main phyla of the oral microbiome of healthy subjects (FIG. 1C). The polyphenolic compound was administered to healthy subjects in a pastille form at one pastille three times a day (FIG. 1B). Other healthy subjects were administered a placebo, where the placebo is a pastille without the polyphenolic compound (FIG. 1A).

A pharmaceutical composition comprising a polyphenol and a surfactant/emulsifier is used to modulate the oral microbiome of a subject. 50 mgs of (1E,6E)-1,7-bis (4-hydroxy-3-methoxyphenyl)-1,6-heptadiene-3,5-dione was combined with 5 mgs of surfactants. The composition was encapsulated in a gelatin matrix, and was tested for its ability to modulate the oral microbiome of patients suffering from oral cancer. The pharmaceutical composition was administered in varying doses as a pastille to healthy subjects and to subjects having oral cancer. A single pastille was administered three times a day to patients from both subject groups (FIGS. 1 and 3), and was also administered as two pastilles three times a day to patients from both subject groups (FIGS. 2 and 4). In addition, a placebo control was administered as a pastille to patients from both subject groups. The oral microbiomes of patients receiving the drug or placebo were analyzed for compositions of the microbial populations.

Example 2

Drug Administration

A phase I clinical trial was conducted with a pharmaceutical composition derived from *Curcuma longa* in 12 subjects with oral cancer. (Basak, S. K., et al. (2020), A randomized, phase 1, placebo-controlled trial of APG-157 in oral cancer demonstrates systemic absorption and an inhibitory effect on cytokines and tumor-associated microbes. *Cancer.* 2020; 126(8): 1668-1682. doi: 10.1002/cncr.32644; the entire contents of which are incorporated by reference herein). The pharmaceutical composition comprised a high polarity extract, a medium polarity extract containing polyphenols and a low polarity extract combined in a 3:6:1 ratio by weight, respectively, in a hydrogel, i.e., a gelatin/glycerin gel. Two different doses of the drug were administered in pastille form, 100 mg and 200 mg. Each dose of the drug was delivered once an hour for three consecutive hours. The drug was maintained in the mouth until dissolved. Blood and saliva were collected at 0 hr (pretreatment) and at 1, 2, 3, and 24 hrs post-treatment. Salivary samples were analyzed for microbial populations in response to the drug. Salivary samples were also analyzed for the expression of cytokines. In a diseased state, changes in the microbial population can lead to an increase in the relative population of pathogenic organisms which, in turn, can unleash the chronic inflammatory response as evidenced by the change in the cytokine levels and more specifically, but not limited to, an increase in pro-inflammatory cytokines.

16S Ribosomal RNA Analysis of Patient Samples

The microbiome composition was analyzed for the saliva samples utilizing DNA extraction and sequencing of the 16S ribosomal RNA gene as described by Jacobs et al., "Microbial, metabolomic, and immunologic dynamics in a relapsing genetic mouse model of colitis induced by T-synthase deficiency" *Gut Microbes* 8:1, 1-16(2017) DOI: 10.1080/19490976.2016.1257469. In brief, bacterial DNA was extracted using the QIAGEN (cat #12955-4) Powersoil kit with bead beating. The V4 region of the 16S gene was amplified and barcoded using 515f/806r primers then 250×2 bp sequencing was performed on an Illumina HiSeq 2500. Raw data were processed using DADA2 scripts in R platform and amplicon sequence variants (ASV) were identified by closed reference picking against the Silva database (Callahan et al. "DADA2: High-resolution sample inference from Illumina amplicon data" Nat Methods 2016 July; 13(7): 581-583 doi: 10.1038/nmeth.3869).

Statistical Analyses

For the microbiome, alpha diversity metrics included Faith's phylogenetic diversity (Faith's PD) metric, Chaol, and Shannon index. The significance of differences in alpha diversity was calculated by a two-tailed t-test. Beta diversity was calculated using square root Jensen-Shannon divergence and visualized by principal coordinates analysis. Adonis, a permutational analysis of variance, was performed using 10,000 permutations to test for differences in square root Jensen-Shannon divergence distances across diet and groups. Association of microbial genera with cancer, treatment, time point, and dose were evaluated using DESeq2 in R, which employs an empirical Bayesian approach to shrink dispersion and fit non-rarified count data to a negative binomial model (Love et al. "Moderated estimation of fold change and dispersion for RNA-seq data with DESeq2" *Genome Biology* 15, 550 (2014) doi.org/10.1186/s13059-014-0550-8). P-values for differential abundance were converted to q-values to correct for multiple hypothesis testing (<0.05 for significance).

Cytokine Analysis in Saliva

Figures 6A, 6B, 6C:
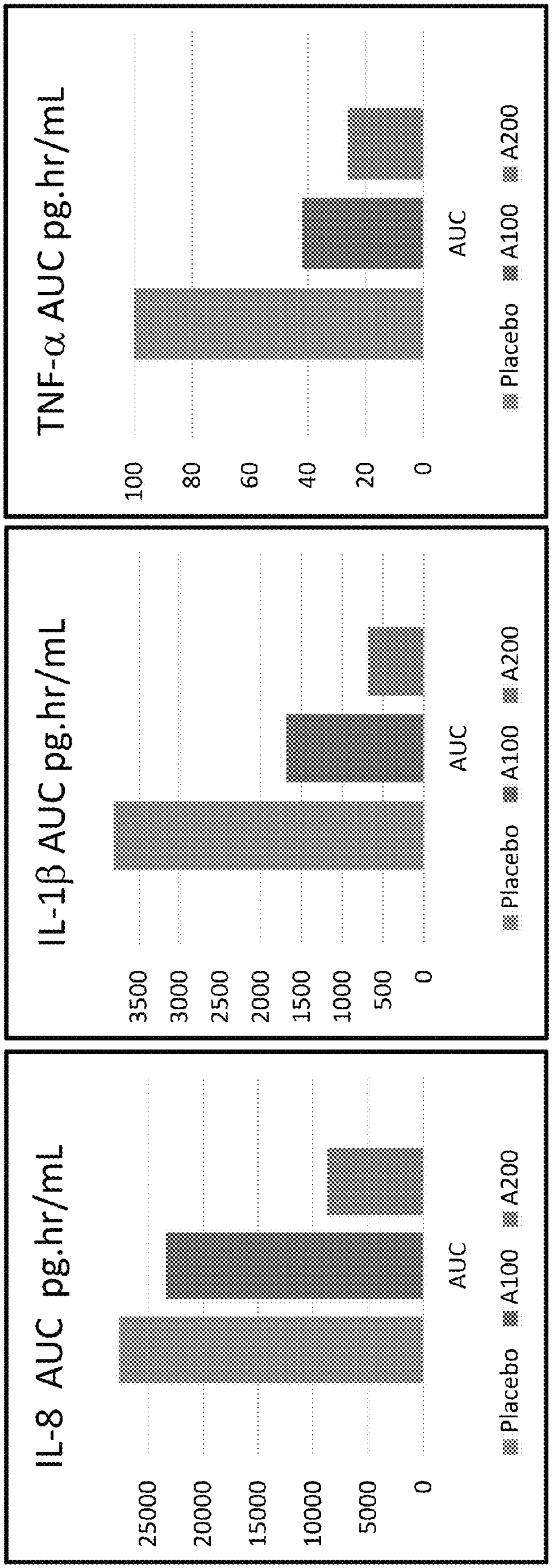
FIGS. 6A-6C demonstrate dose-dependent cytokine downregulation (IL-8 (FIG. 6A), IL-1B (FIG. 6B), TNF-α (FIG. 6C)) in the saliva of the patients (pooled data) whose F/B ratio increased upon administration of a drug containing polyphenol (AV1016).

Cytokine (IL-1β, IL-2, IL-6, IL-8, IL-10, IL-12p70, IL-13, IL-4, INF-γ, TNF-α and GM-CSF) levels were evaluated in salivary cell-free supernatant and salivary cells of subjects by the multiplex ELISA method (FIG. 6).

The salivary microbiome and three select cytokine levels in the saliva sample of a specific patient from the clinical trial is summarized in FIG. 7. The patient is a 64-year old male with a floor of the mouth cancer. The patient received 3×200 mg of the pharmaceutical composition comprising a high polarity extract, a medium polarity extract containing polyphenols and a low polarity extract combined in a 3:6:1 ratio by weight, respectively, in a hydrogel carrier. The direction of the changes in the microbiome population and cytokine levels are both in the favorable direction showing the therapeutic effect of the pharmaceutical composition.

Example 3

This Example both re-presents certain data from Example 2 and provides additional data. Reference is made to Supplementary Figures from Basak, S. K., et al. (2020), A randomized, phase 1, placebo-controlled trial of APG-157 in oral cancer demonstrates systemic absorption and an inhibitory effect on cytokines and tumor-associated microbes. *Cancer.* 2020; 126(8): 1668-1682. doi: 10.1002/cncr.32644; the entire contents of which are incorporated by reference herein.

APG-157 Treatment Did not Result in Local or Systemic Toxicity

Figure 1B:
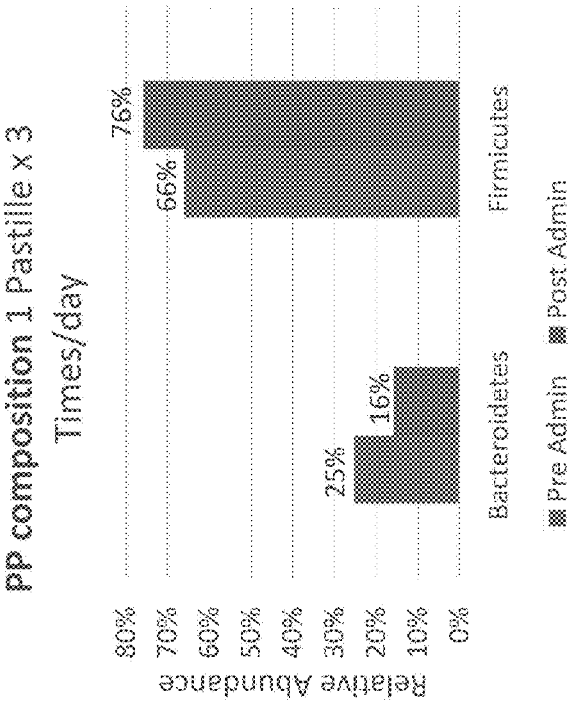
Figure 1C:
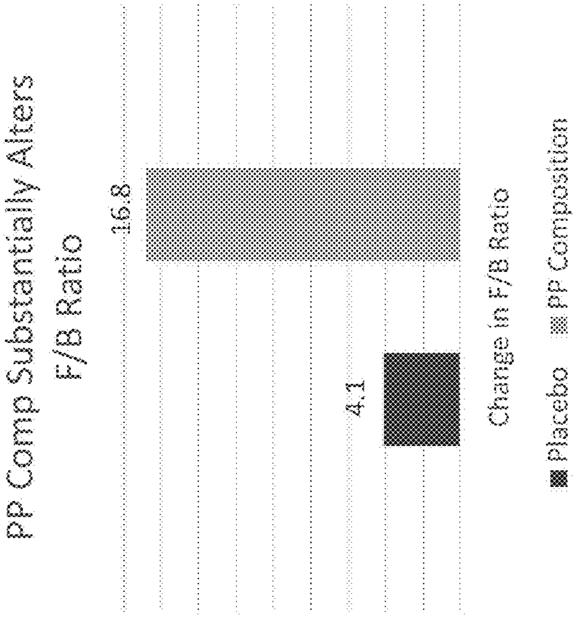
Figure 2B:
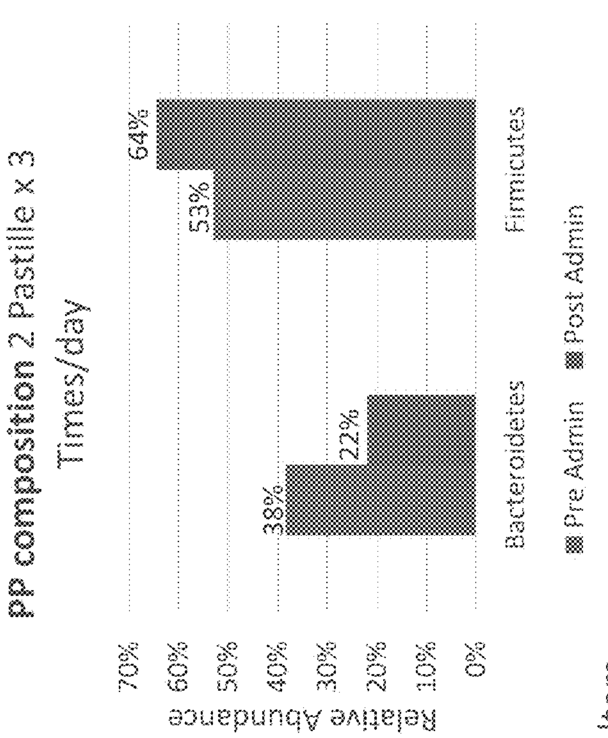
FIGS. 2A-2C demonstrate the effect of a polyphenolic (PP) compound on the relative population of main phyla of the oral microbiome of healthy subjects (FIG. 2C). The polyphenolic compound was administered to healthy subjects in a pastille form at two pastilles three times a day (FIG. 2B). Other healthy subjects were administered a placebo, where the placebo is a pastille without the polyphenolic compound (FIG. 2A). The effect of dosing is shown by a higher change in the ratio of Firmicutes to Bacteroidetes (F/B ratio) compared to a single pastille dose (FIG. 2C and FIG. 1C).
Figure 2C:
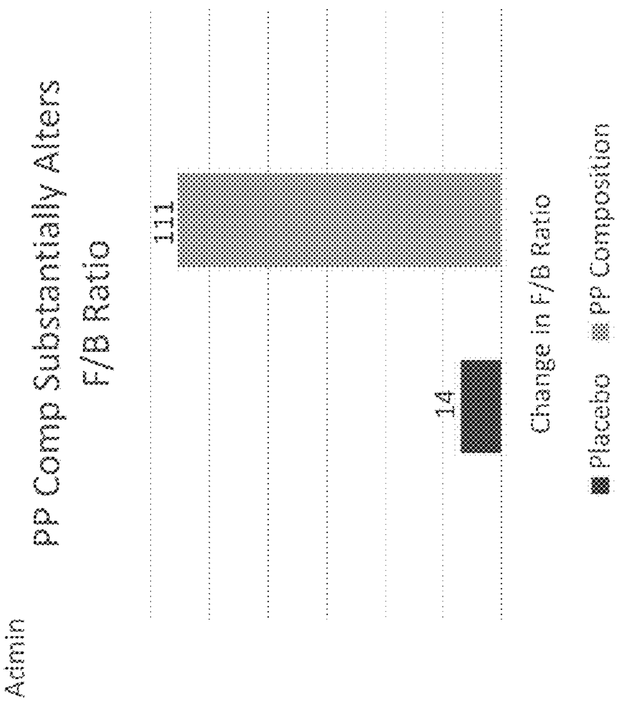
Figure 2A:
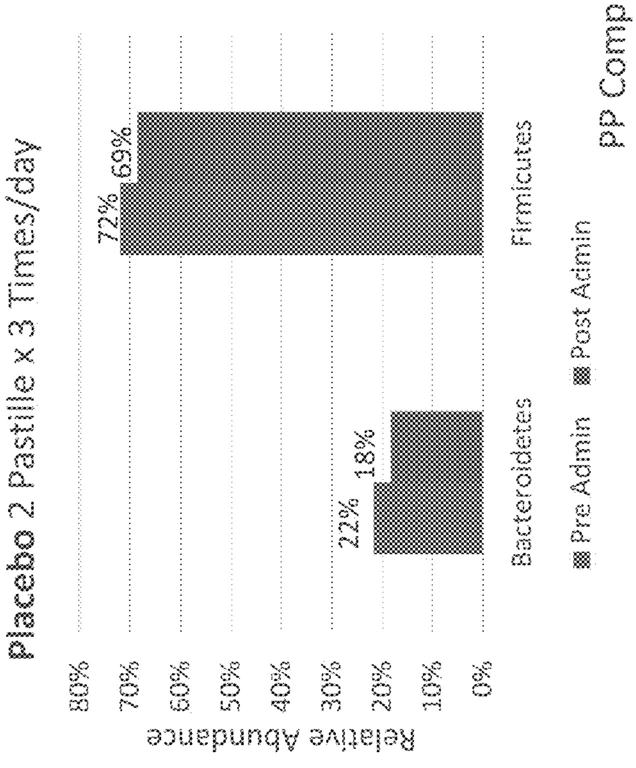

A total of 13 normal subjects and 12 subjects with oral cancer participated in the study (age range, 33-75 years) (FIG. 8) (see Supporting FIG. 1 of Basak, S. K., et al.). Four subjects in the placebo group and 3 subjects in the APG-157 group withdrew from the study. Of the 25 subjects, 12 received placebo control and 13 received active drug APG-157 (FIG. 8). None of the subjects reported adverse effects from any of the procedures used in the current study.

Electrocardiogram results evaluated for PR wave delay did not demonstrate a significant delay in any of the subjects, except in 1 normal subject who received 100 mg of APG-157, in whom a PR delay of 24 milliseconds at 24 hours after treatment was observed. This was deemed to be within the normal range of variation. The serum samples from the 25 subjects did not demonstrate any abnormalities with regard to blood counts, electrolytes, or liver or kidney functions except for a preexisting condition or some minor variations.

Transoral APG-157 Treatment Results in Systemic Curcumin Absorption

Figure 9A:
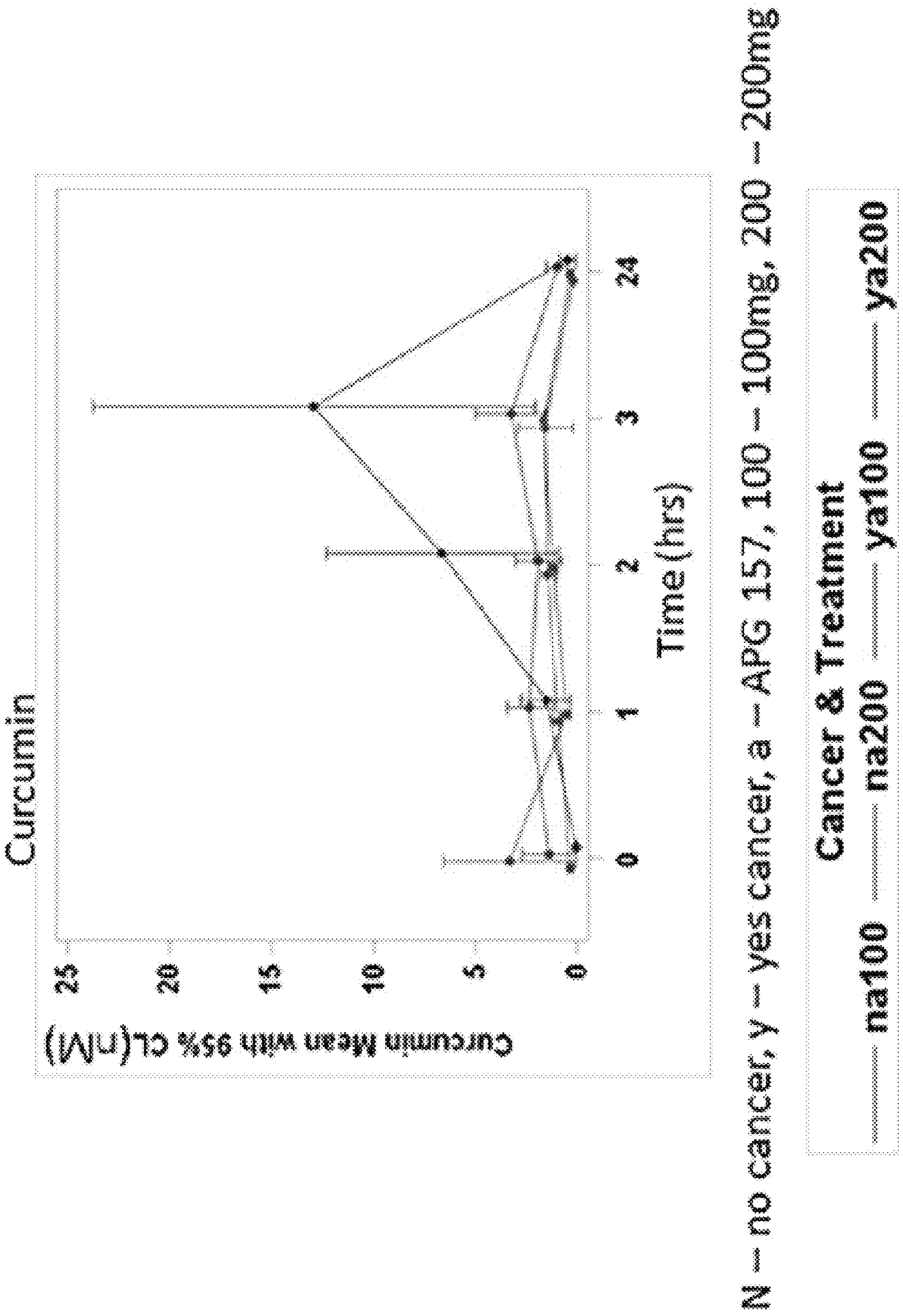
Figure 9B:
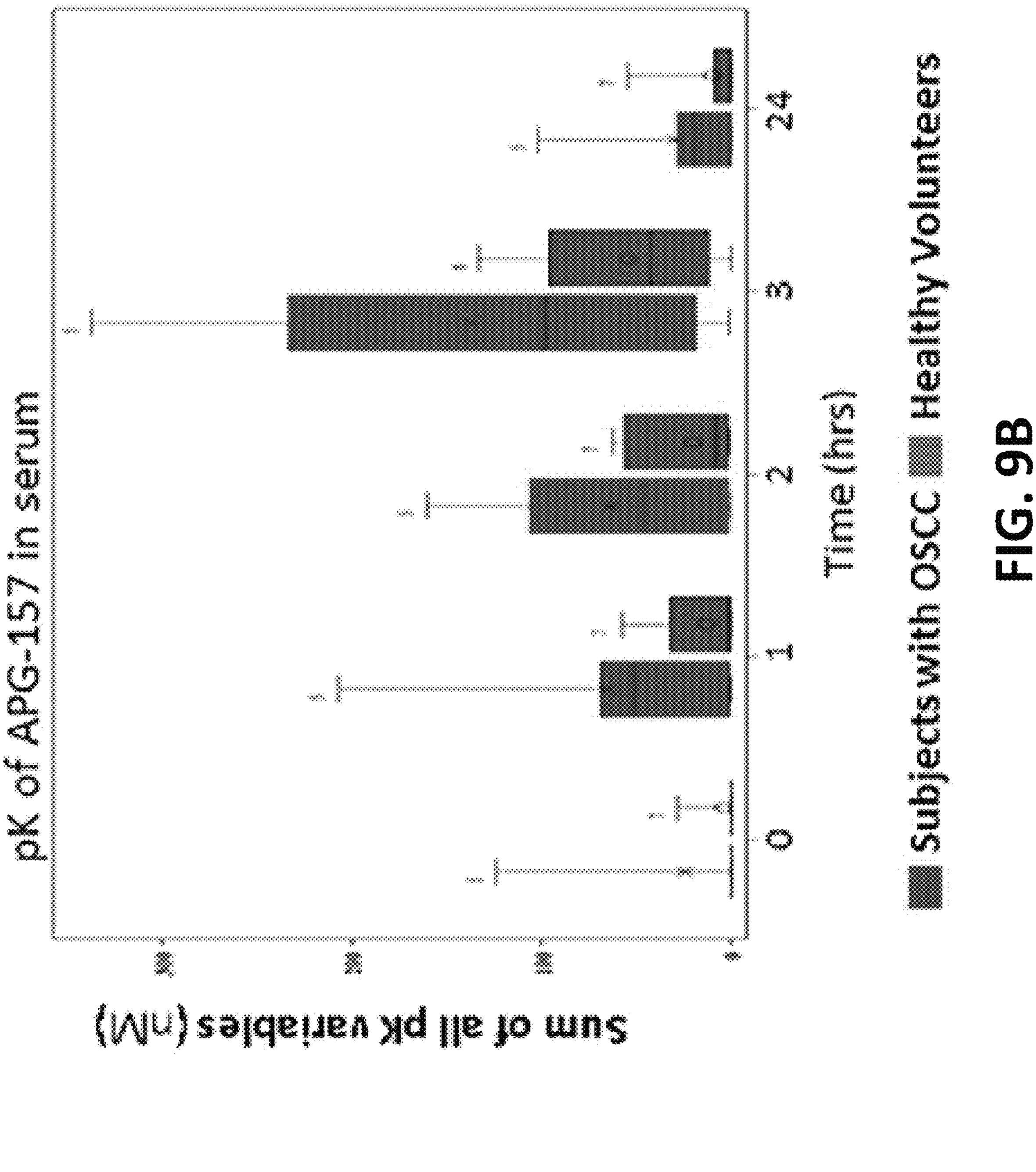

Despite considerable variation between subjects with regard to measured concentrations, curcumin, dimethoxycurcumin (DMC), bisdemethoxycurcumin (BDMC), tetrahydrocurcumin (THC), and glucuronidated curcumin (CG) were detected in the sera of all subjects after treatment with APG-157 at the 2-hour, 3-hour, and 24-hour time points. As expected, there generally were higher serum concentrations in the group treated with 200 mg of APG-157 compared with those receiving the 100-mg dose, indicating a dose-dependent effect. Curcuminoids were not detected in the sera from individuals receiving placebo. Curcumin concentrations were between 0.5 and 2 nM at the 1-hour time point, rose to a maximum of 1.5 to 13 nM at 3 hours, and declined at the 24-hour time point (FIG. 9A). The temporal display of the summed concentrations of all 5 compounds overcame to a large extent the between-subject variability and more clearly demonstrated that peak curcuminoid concentrations were reached at the 3-hour time point (FIG. 9B). This result also suggests higher concentrations of the compounds in sera from patients with cancer compared with healthy controls, although caution should be exercised herein because of the relatively small sample size.

Figure 9D:
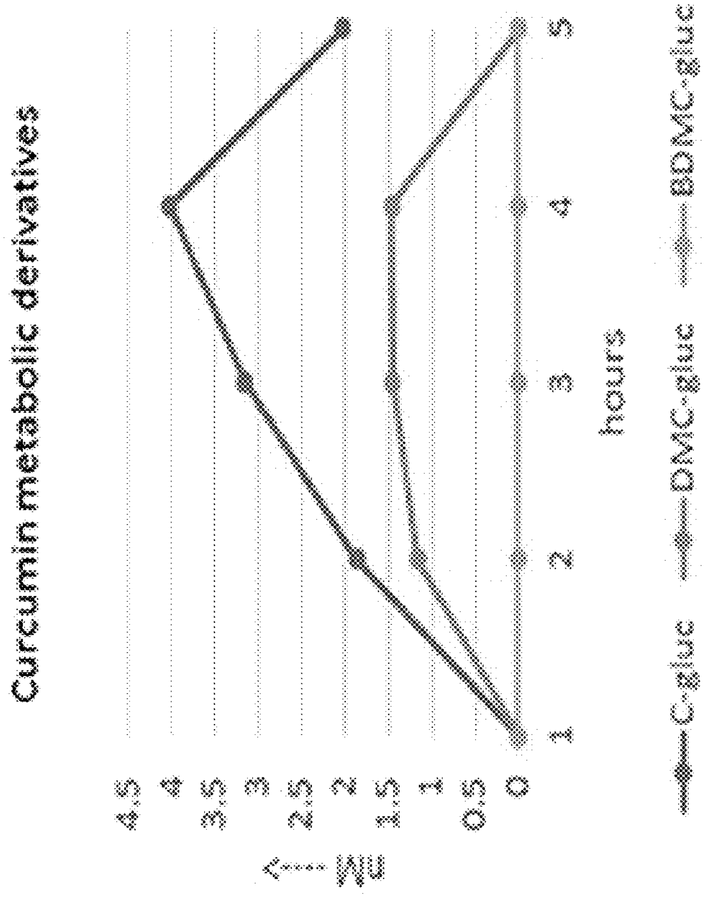
Figure 9C:
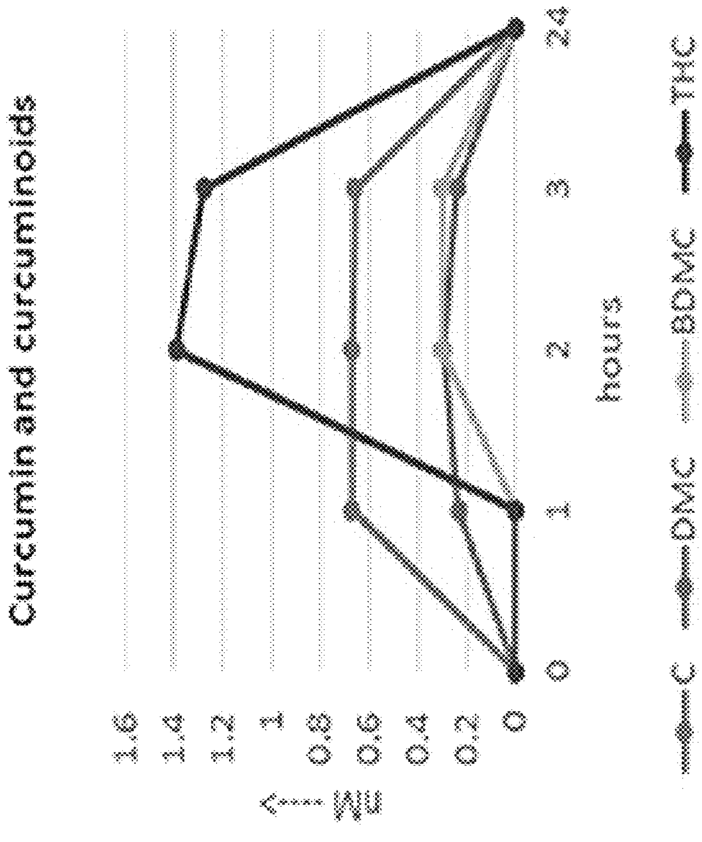
Figure 9E:
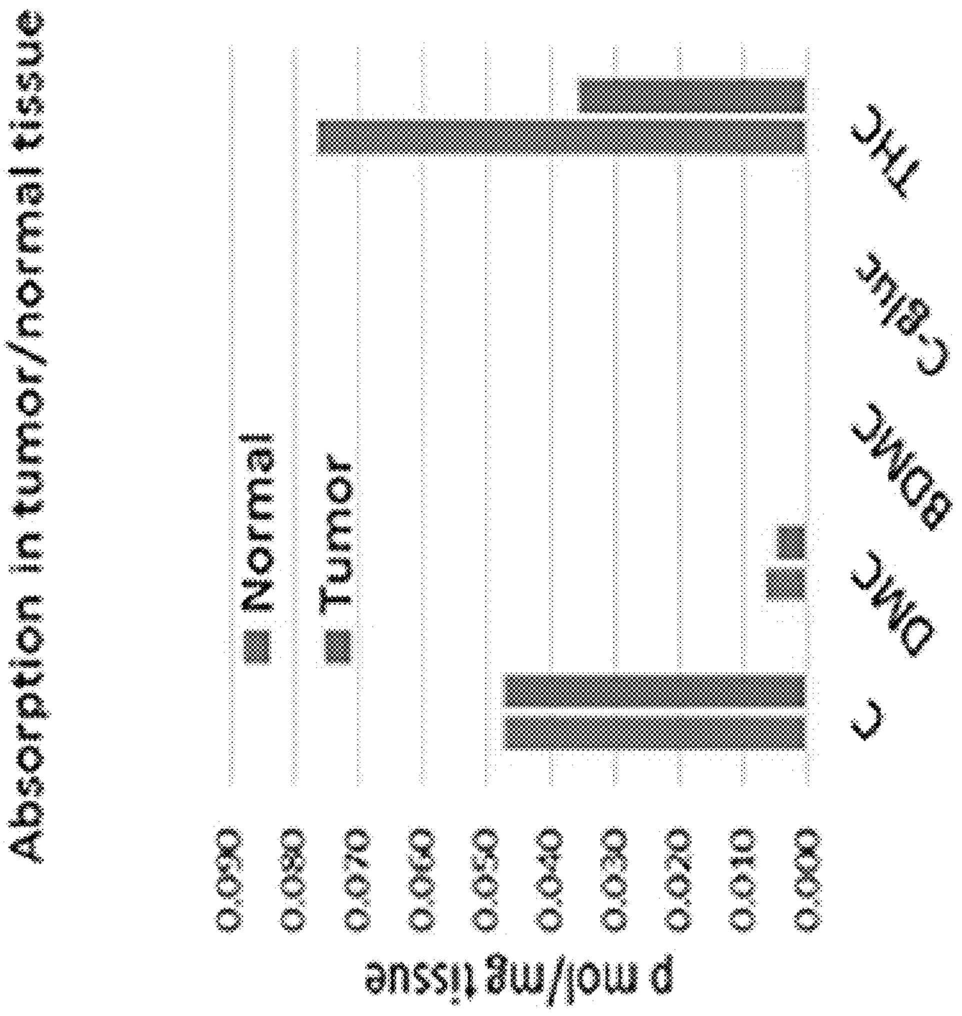

One of the cancer subjects (patient 1*) who was treated with APG-157 underwent surgery for tumor removal 24 hours after treatment, and his blood and normal and tumor tissues were evaluated. The results demonstrated that the temporal serum profiles of curcumin, DMC, BDMC, and THC concentrations in this patient reached a maximum of up to 1.4 nM between 1 to 3 hours after treatment (FIG. 9C), whereas the temporal profiles of CG and DMCG in the sera reached a maximum of up to 4 nM and were slightly delayed, peaking between 3 to 24 hours after treatment (FIG. 9D). Curcumin and THC were the major curcuminoids detected in the tumor and adjacent normal tissues from this individual, with smaller amounts of DMC and undetectable amounts of BDMC and the glucuronide derivatives (FIG. 9E). These results demonstrated that transoral delivery of APG-157 results in the absorption of curcumin and its analogs in both the blood and oral tissues.

APG-157 Treatment Leads to a Reduction in Salivary Pro-Inflammatory Cytokine Concentrations FIG. 10 shows decreased cytokine concentrations of IL-8, IL-1β, and TNF-α among patients with cancer treated in the placebo versus APG-157 groups. The present inventors did not observe statistically significant differences between normal subjects, who expressed low levels of cytokines, and patients with cancer. The results for all the cytokines for both the normal subjects and patients with cancer treated with placebo or APG-157 are included in Supporting FIG. 2 of Basak, S. K., et al.

Figure 3B:
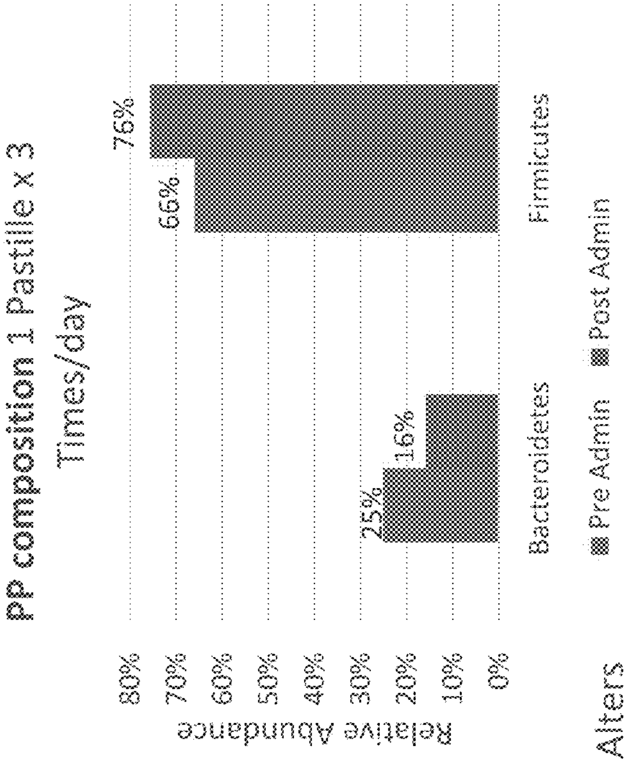
FIGS. 3A-3C demonstrate the effect of a polyphenolic (PP) compound on the relative population of the main phyla of the oral microbiome of subjects having oral cancer (FIG. 3C). The polyphenolic compound was administered to subjects having oral cancer in a pastille form at one pastille three times a day (FIG. 3B). Other subjects having oral cancer were administered a placebo, where the placebo is a pastille without the polyphenolic compound (FIG. 3A).
Figure 3C:
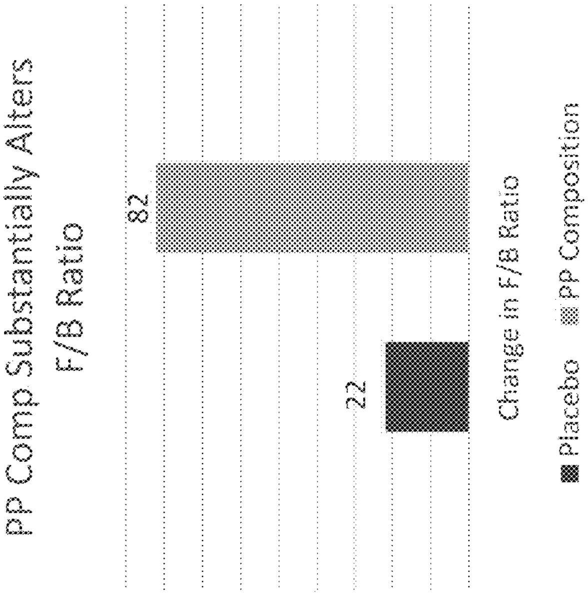
Figure 3A:
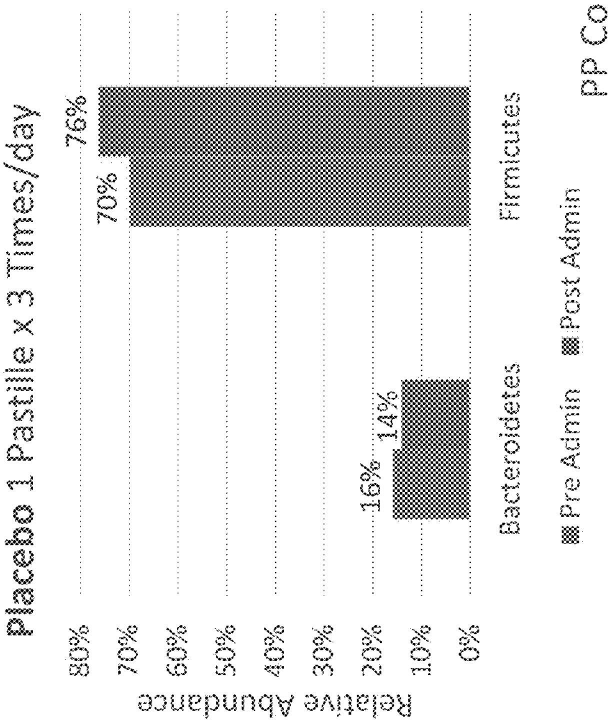
Figure 4A:
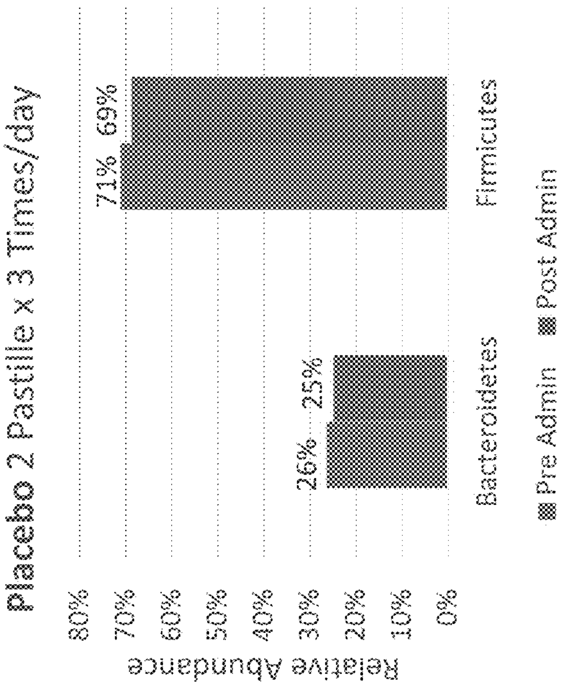
FIGS. 4A-4C demonstrates the effect of a polyphenolic (PP) compound on the relative population of the main phyla of the oral microbiome of subjects having oral cancer (FIG. 4C). The polyphenolic compound was administered to subjects having oral cancer in a pastille form at two pastilles three times a day (FIG. 4B). Other subjects having oral cancer were administered a placebo, where the placebo is a pastille without the polyphenolic compound (FIG. 4A). The effect of dosing is shown by a higher change in the ratio of Firmicutes to Bacteroidetes (F/B ratio) compared to a single pastille dose (FIG. 4C and FIG. 3C).
Figure 4B:
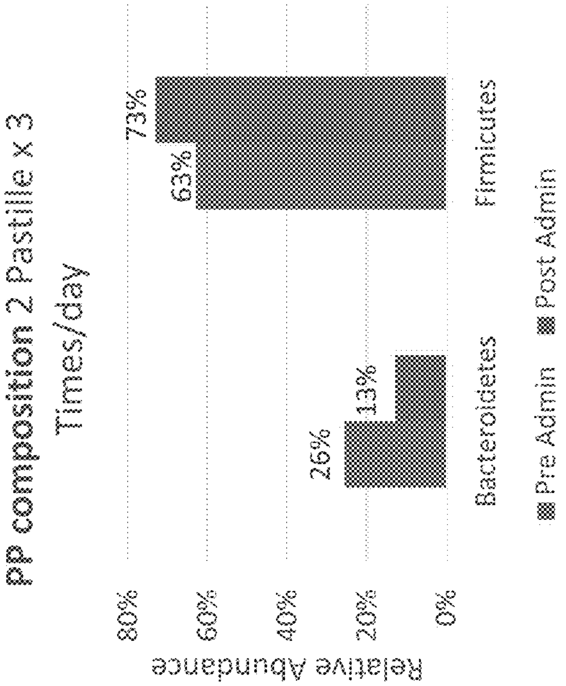
Figure 4C:
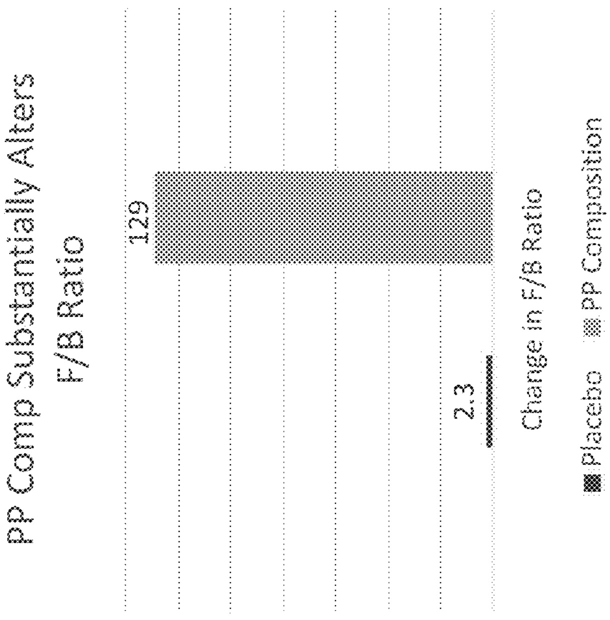

Evaluation of salivary samples from cancer subject 1*, who underwent surgery after treatment, demonstrated reductions in inflammatory cytokine levels of IL-12p70, IL-6, and TNF-α and an increase in the levels of IFN-γ, IL-10, IL-2, and IL-1β at 3 hours in the salivary supernatant fluid samples treated with APG-157 (see Supporting FIG. 3 of Basak, S. K., et al.). The reduction in cytokine concentrations (IL-6, IL-8, IFN-γ, IL-10, granulocyte-macrophage colony-stimulating factor, IL-12p70, and TNF-α) in the cells and supernatant fluid samples 24 hours after treatment might be due to continued drug treatment after 3 hours by this subject, attributed to delayed absorption secondary to the large tumor and dry mouth conditions.

Reduction in *Bacteroides* in Salivary Cells Treated With APG-157

There was a statistically significant difference noted with regard to microbial composition as measured by beta diversity between patients with cancer and control subjects (FIG. 11A). There was no statistical difference noted with regard to any alpha diversity metric. However, there were many differences noted when comparing the relative abundances of patients with cancer versus control subjects at both the phyla and genus levels (FIG. 11B). Differential abundance testing was performed at the genus level to compare patients with cancer with control subjects. FIG. 11D shows all the genera that were found to be statistically different (q value<0.05) between patients with cancer and control subjects. Overall, there were 33 genera that were found to be different between the 2 groups, with Fusicatenibacter, Dorea, Dialister, Ruminococcus, and an unknown genus belonging to the Ruminococcaceae family comprising the genera with the highest relative abundance in patients with cancer compared with control subjects.

Similar to the differences observed between patients with cancer and controls, there also was a significant difference in the microbial composition noted between subjects who received APG-157 compared with placebo when controlling for covariates including cancer and timing of sample collection (FIG. 12A). There was no statistical difference noted with regard to any alpha diversity metric between patients treated with placebo versus APG-157, and the compositional makeup 24 hours after treatment is summarized in FIG. 12B. Differential abundance testing demonstrated that 5 genera were statistically different between subjects treated with placebo versus APG-157 when controlling for the presence of cancer and the timing of sample collection (FIG. 12C). *Bacteroides* was the genus found to have the greatest relative abundance and demonstrated a clear decrease after treatment with APG-157 across time (FIG. 12D). Compared with baseline values before treatment, APG-157 treatment resulted in a 56% decrease in *Bacteroides* species 24 hours after treatment with APG-157.

Analysis of the pooled data regarding the microbial population in patients with cancer who were treated with APG-157 and placebo demonstrated that there was a dose-dependent reduction in the ratio of Firmicutes to Bacteroidetes in subjects treated with APG-157 compared with those receiving placebo (data not shown). The ratio of Firmicutes to Bacteroidetes for subjects receiving 100 mg of placebo and 100 mg of APG-157 was 22% versus 82%, respectively, and was 2.3% versus 129%, respectively, for subjects receiving 200 mg of placebo and 200 mg of APG-157, indicating a concentration-dependent reduction in the *Bacteroides* population after treatment with APG-157.

APG-157 Treatment Results in an Alteration in the Gene Expression Pattern in Tumor Tissue RNA-Seq analysis was performed in duplicates from FFPE normal and tumor tissues collected 2 months prior to treatment and after treatment. Due to the heterogeneous cell composition of the biopsies, gene expression-based deconvolution was performed using 2 distinct algorithms. Transcriptionally significant differences in cell and tissue composition between the adjacent normal tissue and the tumor tissue, as well as between the pretreatment biopsy and posttreatment tumor samples, were determined (FIG. 13A). Gene expression-based tissue deconvolution principal component analysis demonstrated that a large percentage of variability could be explained by principal component 1 and is due to the difference between normal tissue and pretreatment and posttreatment tumor samples (FIG. 13B). Both Gene Expression Deconvolution Interactive Tool (GEDIT) and Signature Visualization Tool (SaVanT) perform a supervised deconvolution against a reference matrix of choice, and SaVanT in addition performs an analysis of variance test for differences in tissue type abundance between samples. FIG. 13B shows the differences in tissue type composition estimated by GEDIT, which sums the estimates to 1 and therefore the results strongly depend on the number of tissues provided in the reference set. The highest percentage of signature genes detected in the normal tissue was characteristic of skeletal muscle (FIG. 13C). However, the pretreated tumor biopsy cells were enriched for bronchial epithelial and adenocarcinoma cells, and the posttreatment tumor samples demonstrated upregulation of adipocyte-specific and cardiac myocyte-specific genes.

The same analysis was performed using only the immune cell types to estimate potential immune cell infiltration in tumor or healthy tissue. Gene deconvolution for immune cell subtypes demonstrated differences in B-cell and T-cell subpopulations in the normal versus tumor tissues (see Supporting FIG. 4A of Basak, S. K., et al.). A similar analysis using SaVanT and selected tissues from the GTEx data-base also was performed. Unlike GEDIT, SaVanT out-puts scores rather than the percentages of cell populations, and the scores do not usually add up to 1. Using a built-in functionality, analysis of variance for significant differences between tissue abundances, demonstrated a significantly higher abundance of skeletal and esophageal muscle signature in the normal tissue compared with both tumor biopsies (see Supporting FIG. 4B of Basak, S. K., et al.). Conversely, the prebiopsy sample was enriched in the esophageal mucosa signature, whereas the posttreatment tumor biopsy was enriched in a transformed fibroblast tissue signature. Thus, a differential effect on gene expression was observed in posttreatment tumor cells compared with the prebiopsy tumor cells.

Differential Gene Expression

Figure 5:
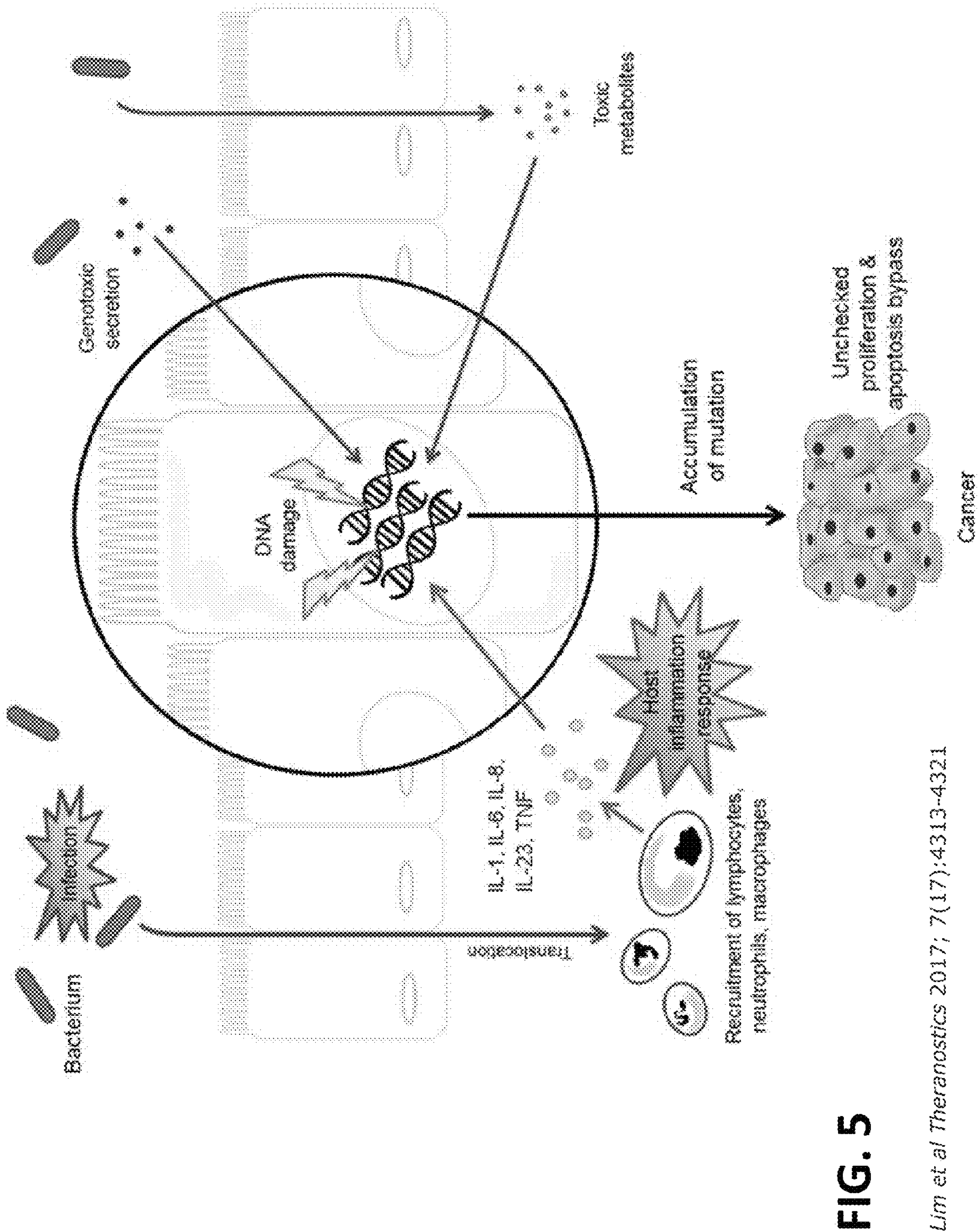
FIG. 5 demonstrates a mode of microbial influence on the pathogenesis of oral cavity and oropharyngeal cancers (Lim Y, et al., Oral Microbiome: A New Biomarker Reservoir for Oral and Oropharyngeal Cancers. *Theranostics* 2017; 7(17): 4313-4321. doi: 10.7150/thno.21804).

Using DESeq2 genes with a Benjamini-Hochberg adjusted P value of <0.01, an absolute fold change ≥2 was selected. In prebiopsy tumor tissue, gene ontology enrichment analysis demonstrated a significant upregulation of genes associated with cell adhesion, cell division, and the cell cycle (see Supporting FIG. 5A of Basak, S. K., et al.), and downregulation of genes related to metabolism, energy, and muscle development in prebiopsy tumor cells (see Supporting FIG. 5B of Basak, S. K., et al.). This result confirmed an increased muscle tissue signature in the normal tissue sample compared with the prebiopsy sample. Similarly, these genes and their pathways were upregulated or downregulated in posttreatment tumor tissue compared with adjacent normal tissue (see Supporting FIGS. 5C and 5D of Basak, S. K., et al.). Although the number of significantly different genes between the pretreatment and posttreatment biopsies was lower (data not shown), some of the upregulated genes in the posttreatment tumors were involved in muscle system or vascular development, similar to the genes upregulated in normal tissues (see Supporting FIGS. 5E and 5F of Basak, S. K., et al.). Thus, the results demonstrated a differential expression of genes after treatment with APG-157 and there was downregulation of genes related to the cell cycle and upregulation of genes related to skeletal muscle development observed in the posttreatment tumor cells.

Analysis of the p53 sequence in cancer subject 1* demonstrated a conversion of amino acid 72 proline/proline homozygous alleles in the prebiopsy specimen to arginine/proline heterozygous alleles in the post-treatment normal and tumor tissues (see Supporting FIG. 6 of Basak, S. K., et al.). This possibly could be due to APG-157-mediated killing of proline/proline-containing cells in the heterozygous tumor cell population.

Recruitment of Immune Cells to the Tumor Microenvironment After Treatment With APG-157

Hematoxylin and eosin staining of the prebiopsy tumor sample demonstrated the presence of adipocytes, skeletal muscle, nerve cells, and lymphocytes (FIG. 14A). Multiplex immunofluorescence staining showed the presence of scattered CD8-positive cells (FIG. 14B). However, cells that were positive for CD4, PD-1, and PD-L1 were not observed.

After APG-157 treatment, normal tissue (adjacent to the resected tumor) demonstrated the presence of adipocytes, skeletal muscle, nerve cells, and lymphocytes (FIG. 14C). Immunofluorescence staining showed positivity for CD8-positive cells and a few CD4-positive cells (FIG. 14D). There was no staining for PD-1 or PD-L1 ex-pression noted. After treatment with APG-157, hematoxylin and eosin staining of oral tumor tissue demonstrated the presence of salivary gland cells, tumor cells, and fibrous stroma (FIG. 14E). There was a marked increase in the expression of CD8-positive and CD4-positive cells (FIG. 14F). Many of these T cells also were found to be positive for PD-1 expression. Finally, PD-L1 positivity in the tumor cells that were absent in prebiopsy tumor cells also was observed.

Analysis of left and right neck lymph node biopsies after treatment with APG-157 demonstrated the presence of CD8-positive and CD4-positive cells in the paracortex, PD-1-positive staining in the germinal center, and PD-L1-positive staining in the paracortex (see Supporting FIGS. 7A-7D of Basak, S. K., et al.). These results indicated recruitment of T cells to the tumor microenvironment, possibly attributed to APG-157 treatment.

Materials and Methods

Study Population

The investigation was performed after approval from the institutional review board (IRB) of the Veterans Administration Greater Los Angeles Healthcare System (VAGLAHS) in Los Angeles, California. Subject recruitment and drug treatments followed the protocols approved by the VAGLAHS IRB. The normal and cancer cohorts were recruited from the ear, nose, and throat clinics at VAGLAHS. Inclusion criteria were age >18 years, English fluency, and no history of prior chemotherapy or radiotherapy, or inflammatory conditions of the oral cavity or oropharynx. Patients with cancer had biopsy proven OSCC. One of the patients with cancer (patient 1*) was included in the study with advanced cancer of the floor of the mouth and underwent surgery for tumor removal 24 hours after the completion of the study. His prestudy biopsy and poststudy surgically removed normal and tumor tissues were available to determine the effect of treatment on tumor cells.

Cancer staging and exclusion criteria of the study are included in detail in the Supporting Materials.

Study Product

APG-157, which contains turmeric extract, is a proprietary, patent-pending, drug product developed by Aveta Biomics Inc. The drug substance, derived from the plant *Curcuma longa*, differs from other turmeric products in its use of a complete unfractionated herb extract, and is encapsulated in a soft lozenge, a hydrogel-based drug delivery system. APG-157 slowly disintegrates in the oral cavity over 15 to 20 minutes to release the drug substance. The drug substance is a precise, rational combination of multiple molecules derived from *Curcuma longa* wherein curcumin is the principal component. It is produced by the biofractionation of the rhizome of *Curcuma longa* under current good manufacturing practice (cGMP) conditions to meet US Food and Drug Administration Chemistry, Manufacturing, and Controls guidance ensuring the consistency and quality of the pharmaceutical grade product. Each APG-157 lozenge contains 100 mg of the drug substance.

Study Design and Procedure

Two different dosages of the drug (APG-157) or placebo control gelatin pastilles, 3×100 mg and 3×200 mg, were tested (FIG. 8). A total of 32 subjects were enrolled, and 25 completed the study (see Supporting FIG. 1A of Basak, S. K., et al.): 13 normal individuals (4 in the 100-mg placebo control group and 3 in the 100-mg APG-157 treatment group and 2 in the 200-mg placebo group and 4 in the 200-mg APG-157 treatment group) and 12 patients with oral cancer (2 in the 100-mg placebo control group and 3 in the 100-mg APG-157 treatment group and 4 in the 200-mg placebo control group and 3 in the 200-mg APG-157 treatment group). The drug was delivered transorally each hour for 3 consecutive hours for a 1-day treatment. Blood and saliva were collected before treatment and each hour after treatment (3 collections), and 1 sample was collected 24 hours after treatment (FIG. 8).

Blood Collection

A nurse practitioner collected blood using an IRB-approved procedure (FIG. 8). Serum was isolated using the appropriate collection tube. At least 5 mL of blood was collected at each time point to obtain 2 mL of serum. Collections caused minimal pain and the subjects did not report any after effects.

Saliva Collection

Saliva was collected before and after treatment at 1-hour intervals (3 collections) (FIG. 8). Briefly, 10 mL of saliva was collected in 50-mL tubes and kept in ice until completion of the 3-hour collection. The samples were centrifuged (500×g for 15 minutes) and the supernatant fluid and pellets were frozen in aliquots and stored at −80° C. until analysis.

Evaluation of Toxicity and/or Adverse Effects

Electrocardiograms were performed before treatment and 24 hours after treatment and read by a VAGLAHS cardiologist. Aliquots of serum (200 μL) were used for kidney and liver function tests at the department of pathology and laboratory medicine of the VAGLAHS.

Measurement of Curcumin and Analogs in Blood and Tissue

Serum and tissue samples were evaluated for curcumin, DMC, bisdemethoxycurcumin (BDMC), tetrahydro-cur cumin (THC), glucuronidated curcumin (CG), DMC-glucuronide (DMCG), and BDMC-glucuronide (BDMCG) concentrations with hexadeuterated curcumin as an internal standard using a highly sensitive combined liquid chromatography/mass spectrometry method as described in the Supporting Materials.

Cytokine Analysis

The preparation of salivary cell and supernatant fluid samples and the measurement of cytokine concentrations were performed following an established protocol using the Meso Scale discovery platform.

Microbiome Profiling

To determine the oral microbial community composition, salivary cells were assayed using the 16S rRNA sequence. Extraction and sequencing of the 16S rRNA gene were performed as previously described at Jacobs J P, Lin L, Goudarzi M, et al. Microbial, metabolomic, and immunologic dynamics in a relapsing genetic mouse model of colitis induced by T-synthase deficiency. *Gut Microbes*. 2017; 8:1-16.

RNA-Seq Analysis

Formalin-fixed, paraffin-embedded (FFPE) prebiopsy tissues and tissue (tumor and adjacent normal tissue) after APG-157 treatment from one of the patients with cancer was evaluated for gene expression by RNA-Seq analysis using an established protocol.

Multiplex Immunofluorescence Analysis

The normal, tumor, and lymph node FFPE tissues from the patient with cancer were stained for hematoxylin and eosin and were evaluated for T cells (CD4 and CD8 cells), PD-L1, and PD-1 expression by established histology and immunostaining methods.

Statistical Analysis

Salivary cytokine data (IL-6, IL-8, TNF-α, and other cytokine levels) were analyzed using a Fisher exact test. Chi-square and Student t tests were performed for the RNA-Seq data. For the microbiome, alpha diversity metrics included the Faith phylogenetic diversity metric, Chao1 function, and Shannon index. The significance of differences in alpha diversity was calculated using a 2-tailed Student t test. Beta diversity was calculated using square root Jensen-Shannon divergence and visualized using principal coordinates analysis. Adonis, a permutational analysis of variance, was per-formed using 10,000 permutations to test for differences in square root Jensen-Shannon divergence distances between drug and placebo controlling for cancer, subject, and timing of the sample collection. Associations between microbial genera with cancer, treatment, time, and dose were evaluated using DESeq2 in R statistical software, which uses an empirical Bayesian approach to shrink dispersion and fit nonrarified count data to a negative binomial model. P values for differential abundance were converted to q values to correct for multiple hypothesis testing (<. 05 for statistical significance).

What is claimed is:

1. A method of treating or inhibiting a dysbiosis of oral microbiome of a subject in need thereof comprising administering a pharmaceutical composition comprising:
(i) one or more polyphenols selected from the group consisting of curcumin, demethoxycurcumin, bisdemethoxycurcumin, and tetrahydrocurcumin;
(ii) one or more high polarity compounds extracted from *Curcuma longa* using a solvent system that has a dielectric constant of greater than 25 or a relative polarity greater than 0.6, wherein the one or more high polarity compounds are selected from the group consisting of peptides, polysaccharides, and proteins;
(iii) one or more non-polar compounds selected from the group consisting of terpenoids, ar-turmerone, α-turmerone, and β-turmerone; and
(iv) one or more emulsifier, surfactant, or a combination thereof;
wherein the dysbiosis of the oral microbiome is determined by a change in a relative abundance of bacterial phyla in comparison to the subject's baseline composition of bacterial phyla prior to administration.

2. The method of claim 1, wherein the one or more high polarity compounds, the one or more polyphenols, and the one or more non-polar compounds isolated from *Curcuma longa* in a 3:6:1 ratio by weight.

3. The method of claim 1, wherein a daily dose of the pharmaceutical composition comprises the one or more polyphenols in an amount between 10 mg and 300 mg.

4. The method of claim 1, wherein the surfactant is selected from the group consisting of a neutral, anionic, cationic, and zwitterionic surfactant.

5. The method of claim 1, wherein the pharmaceutical composition further comprises one or more pharmaceutical excipients, one or more food grade excipients, or a combination thereof.

6. The method of claim 1, wherein the pharmaceutical composition is a mouthwash, drink, pastille, gummy, troche, solid dispersion, paste, a product with oro-mucosal adhesive, spray, oro-mucosal film, or chewing gum.

7. The method of claim 1, wherein the method alters the relative abundance of one or more phyla of the oral microbiome of the subject.

8. The method of claim 7, wherein the one or more phyla are selected from the group consisting of Firmicutes, Bacteroidetes, Proteobacteria, and Actinobacteria.

9. The method of claim 7, wherein a change the changes in the relative abundance of one or more phyla results in a decrease in a level of one or more inflammatory cytokines.

10. The method of claim 9, wherein the subject has a disease characterized by having abnormal levels of one or more inflammatory cytokines elevated above homeostasis levels.

11. The method of claim 9, wherein the change in the relative abundance of one or more phyla results in an improvement in an inflammatory cytokine profile or levels.

12. The method of claim 9, wherein the one or more inflammatory cytokines are selected from the group consisting of interleukins (ILs), tumor necrosis factors (TNFs), Nuclear factor kappa-light-chain-enhancer of activated B cells (NF-kB), NF-kB mediated gene products, NF-kB growth factors, and NF-kB interferons.

13. The method of claim 7, wherein an alteration in the relative abundance of the one or more phyla results in a decrease in the levels of one or more inflammatory cytokines in an oral cavity of the subject.

14. The method of claim 13, wherein the decrease in the levels of one or more inflammatory cytokines in the subject's oral cavity further results in treating an oral precancerous lesion, oral leukoplakia or oral squamous cell cancer.

15. The method of claim 13, wherein the subject has a cancer of the oral cavity associated with elevated cytokine levels, and wherein the administration of the pharmaceutical composition results in a decrease in the levels of one or more inflammatory cytokines in the subject's oral cavity resulting in treating or inhibiting the cancer of the oral cavity.

16. The method of claim 1, wherein the one or more high polarity compounds are isolated from *Curcuma longa* using a solvent system that has a dielectric constant greater than 25.

17. The method of claim 1, wherein the treating or inhibiting of a dysbiosis of the oral microbiome results in the change of the composition of the oral microbiome to healthy state, homeostasis or return to pre-dysbiosis state.

18. The method of claim 1, wherein the dysbiosis of the oral microbiome results in a Firmicutes-to-Bacteroidetes (F/B) ratio of the subject's oral microbiome outside a range of about 1.5 to 3.0.

19. The method of claim 1, wherein the dysbiosis of the oral microbiome is associated with a disease or condition selected from the group consisting of: oral squamous cell carcinoma, glioblastoma, lung cancer, colon cancer, and pancreatic cancer.

20. The method of claim 1, wherein the treating or inhibiting of dysbiosis of the oral microbiome results in a return of a plurality of relative populations of bacterial phyla from dysbiosis to normal or pre-dysbiosis of the microbiome.

21. The method of claim 1, wherein the emulsifier is selected from the group consisting of a neutral, anionic, cationic, and zwitterionic emulsifier.

22. The method of claim 11, wherein an improvement in an inflammatory cytokine profile in saliva of the subject exhibited by reduction of interleukin-6 (IL-6) and tumor necrosis factor-alpha (TNF-α) is associated with a therapeutic benefit in treating oral squamous cell carcinoma.

23. The method of claim 1, wherein the dysbiosis of the oral microbiome is associated with a disease or condition selected from the group consisting of oral precancerous lesions, oral leukoplakia, and oral squamous cell carcinoma.

* * * * *